(12) United States Patent
Christianson et al.

(10) Patent No.: US 12,318,286 B2
(45) Date of Patent: *Jun. 3, 2025

(54) CINCH DEVICE AND METHOD FOR DEPLOYMENT OF A SIDE-DELIVERED PROSTHETIC HEART VALVE IN A NATIVE ANNULUS

(71) Applicant: VDyne, Inc., Maple Grove, MN (US)

(72) Inventors: Mark Christianson, Plymouth, MN (US); Robert Vidlund, Forest Lake, MN (US); David Holtan, Eden Prairie, MN (US); Lucas Harder, Minneapolis, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,098

(22) Filed: Jun. 5, 2023

(65) Prior Publication Data

US 2024/0148496 A1 May 9, 2024

Related U.S. Application Data

(60) Continuation of application No. 17/550,400, filed on Dec. 14, 2021, now Pat. No. 11,712,335, which is a
(Continued)

(51) Int. Cl.
*A61F 2/24* (2006.01)
(52) U.S. Cl.
CPC .............. *A61F 2/2418* (2013.01); *A61F 2/24* (2013.01); *A61F 2/2439* (2013.01); *A61F 2220/0008* (2013.01)

(58) Field of Classification Search
CPC ........ A61F 2/24; A61F 2/2418; A61F 2/2439; A61F 2220/0008
See application file for complete search history.

(56) References Cited

U.S. PATENT DOCUMENTS

| 3,744,060 A | 7/1973 | Bellhouse et al. |
| 4,079,468 A | 3/1978 | Liotta et al. |

(Continued)

FOREIGN PATENT DOCUMENTS

| CN | 107249482 A | 10/2017 |
| CN | 107920862 A | 4/2018 |

(Continued)

OTHER PUBLICATIONS

Extended European Search Report for European Application No. 23215329.6, mailed on Jul. 5, 2024, 5 pages.
(Continued)

*Primary Examiner* — Dinah Baria
(74) *Attorney, Agent, or Firm* — COOLEY LLP

(57) ABSTRACT

The invention relates to anchor channels and subannular anchors for a transcatheter heart valve replacement, and in particular for an orthogonally delivered transcatheter prosthetic heart valve having a annular support frame having compressible wire cells that facilitate rolling and folding the valve length-wise, or orthogonally to the central axis of the flow control component, allowing a very large diameter valve to be delivered and deployed to the tricuspid valve from the inferior vena cava or superior vena cava, or trans-atrially to the mitral valve, the valve having a height of about 5-60 mm and a diameter of about 25-80 mm, without requiring an oversized diameter catheter and without requiring delivery and deployment from a catheter at an acute angle of approach.

12 Claims, 22 Drawing Sheets

Related U.S. Application Data division of application No. 17/236,219, filed on Apr. 21, 2021, now Pat. No. 11,202,706, which is a continuation of application No. PCT/US2020/031390, filed on May 4, 2020.

(60) Provisional application No. 62/843,424, filed on May 4, 2019.

(56) References Cited

U.S. PATENT DOCUMENTS

| | | |
|---|---|---|
| 5,509,428 A | 4/1996 | Dunlop |
| 5,554,185 A | 9/1996 | Block et al. |
| 5,800,531 A | 9/1998 | Cosgrove et al. |
| 5,906,642 A | 5/1999 | Caudillo et al. |
| 6,006,134 A | 12/1999 | Hill et al. |
| 6,290,719 B1 | 9/2001 | Garberoglio |
| 6,312,464 B1 | 11/2001 | Navia |
| 6,449,507 B1 | 9/2002 | Hill et al. |
| 6,458,153 B1 | 10/2002 | Bailey et al. |
| 6,532,388 B1 | 3/2003 | Hill et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,361,189 B2 | 4/2008 | Case et al. |
| 7,442,204 B2 | 10/2008 | Schwammenthal et al. |
| 7,621,948 B2 | 11/2009 | Herrmann et al. |
| 7,648,527 B2 | 1/2010 | Agnew |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 8,628,571 B1 | 1/2014 | Hacohen et al. |
| 8,900,295 B2 | 12/2014 | Migliazza et al. |
| 8,926,694 B2 | 1/2015 | Costello |
| 8,986,370 B2 | 3/2015 | Annest |
| 8,998,982 B2 | 4/2015 | Richter et al. |
| 9,232,995 B2 | 1/2016 | Kovalsky et al. |
| 9,308,086 B2 | 4/2016 | Ho |
| 9,402,720 B2 | 8/2016 | Richter et al. |
| 9,414,915 B2 | 8/2016 | Lombardi et al. |
| 9,468,525 B2 | 10/2016 | Kovalsky |
| 9,504,562 B2 | 11/2016 | Richter et al. |
| 9,526,613 B2 | 12/2016 | Gross et al. |
| 9,597,181 B2 | 3/2017 | Christianson et al. |
| 9,662,202 B2 | 5/2017 | Quill et al. |
| 9,788,946 B2 | 10/2017 | Bobo, Jr. et al. |
| 9,895,219 B2 | 2/2018 | Costello |
| 10,085,834 B2 | 10/2018 | Benson et al. |
| 10,321,995 B1 | 6/2019 | Christianson et al. |
| 10,327,895 B2 | 6/2019 | Lozonschi et al. |
| 10,463,489 B2 | 11/2019 | Christianson et al. |
| 10,485,662 B2 | 11/2019 | Alkhatib |
| 10,485,976 B2 | 11/2019 | Streeter et al. |
| 10,517,718 B2 | 12/2019 | Richter et al. |
| 10,537,425 B2 | 1/2020 | Richter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,653,523 B2 | 5/2020 | Chambers et al. |
| 10,758,346 B1 | 9/2020 | Christianson et al. |
| 10,761,511 B2 | 9/2020 | Chen et al. |
| 10,779,937 B2 | 9/2020 | Vidlund et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund et al. |
| 11,173,027 B2 | 11/2021 | Christianson et al. |
| 11,179,239 B2 | 11/2021 | Vidlund et al. |
| 11,185,409 B2 | 11/2021 | Christianson et al. |
| 11,202,706 B2 | 12/2021 | Christianson et al. |
| 11,234,812 B2 | 2/2022 | Green et al. |
| 11,234,813 B2 | 2/2022 | Perrin |
| 11,253,359 B2 | 2/2022 | Vidlund et al. |
| 11,273,032 B2 | 3/2022 | Christianson et al. |
| 11,273,033 B2 | 3/2022 | Christianson et al. |
| 11,278,437 B2 | 3/2022 | Christianson et al. |
| 11,298,227 B2 | 4/2022 | Vidlund et al. |
| 11,331,186 B2 | 5/2022 | Christianson et al. |
| 11,337,807 B2 | 5/2022 | Christianson et al. |
| 11,344,412 B2 | 5/2022 | Vidlund et al. |
| 11,344,413 B2 | 5/2022 | Christianson et al. |
| 11,712,335 B2 | 8/2023 | Christianson et al. |
| 11,717,399 B2 | 8/2023 | Armer et al. |
| 11,786,366 B2 | 10/2023 | Vidlund et al. |
| 12,138,158 B2 | 11/2024 | Vidlund et al. |
| 12,144,731 B2 | 11/2024 | Vidlund et al. |
| 12,150,852 B2 | 11/2024 | Vidlund et al. |
| 12,186,187 B2 | 1/2025 | Christianson et al. |
| 2002/0138138 A1 | 9/2002 | Yang |
| 2002/0183827 A1 | 12/2002 | Derus et al. |
| 2003/0040808 A1 | 2/2003 | Stack et al. |
| 2003/0055495 A1 | 3/2003 | Pease et al. |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0117009 A1 | 6/2004 | Cali et al. |
| 2004/0167619 A1 | 8/2004 | Case et al. |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0203614 A1 | 9/2005 | Forster et al. |
| 2005/0228472 A1 | 10/2005 | Case et al. |
| 2005/0228495 A1 | 10/2005 | Macoviak |
| 2006/0173524 A1 | 8/2006 | Salahieh et al. |
| 2006/0190075 A1 | 8/2006 | Jordan et al. |
| 2006/0195180 A1 | 8/2006 | Kheradvar et al. |
| 2006/0195183 A1 | 8/2006 | Navia et al. |
| 2006/0229708 A1 | 10/2006 | Powell et al. |
| 2006/0241745 A1 | 10/2006 | Solem |
| 2006/0276887 A1 | 12/2006 | Brady et al. |
| 2007/0016286 A1 | 1/2007 | Herrmann et al. |
| 2007/0073387 A1 | 3/2007 | Forster et al. |
| 2007/0100427 A1 | 5/2007 | Perouse |
| 2007/0239271 A1 | 10/2007 | Nguyen |
| 2008/0065204 A1 | 3/2008 | Macoviak et al. |
| 2008/0071287 A1 | 3/2008 | Goto |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200980 A1 | 8/2008 | Robin et al. |
| 2008/0221672 A1 | 9/2008 | Lamphere et al. |
| 2008/0262592 A1 | 10/2008 | Jordan et al. |
| 2009/0005863 A1 | 1/2009 | Goetz et al. |
| 2009/0048656 A1 | 2/2009 | Wen |
| 2009/0054976 A1 | 2/2009 | Tuval et al. |
| 2009/0132035 A1 | 5/2009 | Roth et al. |
| 2009/0164003 A1 | 6/2009 | Kheradvar |
| 2009/0192601 A1 | 7/2009 | Rafiee et al. |
| 2010/0016894 A1 | 1/2010 | Houard et al. |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0185275 A1 | 7/2010 | Richter et al. |
| 2010/0280591 A1 | 11/2010 | Shin et al. |
| 2010/0298929 A1 | 11/2010 | Thornton et al. |
| 2011/0004237 A1 | 1/2011 | Schneider et al. |
| 2011/0029072 A1 | 2/2011 | Gabbay |
| 2011/0066233 A1 | 3/2011 | Thornton et al. |
| 2011/0071613 A1 | 3/2011 | Wood et al. |

(56) References Cited

U.S. PATENT DOCUMENTS

| | | |
|---|---|---|
| 2011/0137397 A1 | 6/2011 | Chau et al. |
| 2011/0160836 A1 | 6/2011 | Behan |
| 2011/0172784 A1 | 7/2011 | Richter et al. |
| 2011/0224785 A1 | 9/2011 | Hacohen |
| 2011/0245911 A1 | 10/2011 | Quill et al. |
| 2011/0264191 A1 | 10/2011 | Rothstein |
| 2011/0319989 A1 | 12/2011 | Lane et al. |
| 2012/0022605 A1 | 1/2012 | Jahns et al. |
| 2012/0022639 A1 | 1/2012 | Hacohen et al. |
| 2012/0035719 A1 | 2/2012 | Forster et al. |
| 2012/0065723 A1 | 3/2012 | Drasler et al. |
| 2012/0083874 A1 | 4/2012 | Dale et al. |
| 2012/0165928 A1 | 6/2012 | Nitzan et al. |
| 2012/0203336 A1 | 8/2012 | Annest |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0046373 A1 | 2/2013 | Cartledge et al. |
| 2013/0166017 A1 | 6/2013 | Cartledge et al. |
| 2013/0178931 A1 | 7/2013 | Fargahi |
| 2013/0190861 A1 | 7/2013 | Chau et al. |
| 2013/0238089 A1 | 9/2013 | Lichtenstein et al. |
| 2013/0282110 A1 | 10/2013 | Schweich, Jr. et al. |
| 2013/0304197 A1 | 11/2013 | Buchbinder et al. |
| 2013/0304200 A1 | 11/2013 | McLean et al. |
| 2013/0325110 A1 | 12/2013 | Khalil et al. |
| 2013/0338764 A1 | 12/2013 | Thornton et al. |
| 2014/0005778 A1 | 1/2014 | Buchbinder et al. |
| 2014/0012372 A1 | 1/2014 | Chau et al. |
| 2014/0018915 A1 | 1/2014 | Biadillah et al. |
| 2014/0025164 A1 | 1/2014 | Montorfano et al. |
| 2014/0031924 A1 | 1/2014 | Bruchman et al. |
| 2014/0039611 A1 | 2/2014 | Lane et al. |
| 2014/0052237 A1 | 2/2014 | Lane et al. |
| 2014/0067037 A1 | 3/2014 | Fargahi |
| 2014/0121763 A1 | 5/2014 | Duffy et al. |
| 2014/0135908 A1 | 5/2014 | Glozman et al. |
| 2014/0142695 A1 | 5/2014 | Gross et al. |
| 2014/0172077 A1 | 6/2014 | Bruchman et al. |
| 2014/0172083 A1 | 6/2014 | Bruchman et al. |
| 2014/0194983 A1 | 7/2014 | Kovalsky et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0249621 A1 | 9/2014 | Eidenschink |
| 2014/0257466 A1 | 9/2014 | Board et al. |
| 2014/0257467 A1 | 9/2014 | Lane et al. |
| 2014/0276971 A1 | 9/2014 | Kovach |
| 2014/0277342 A1 | 9/2014 | Roeder et al. |
| 2014/0277563 A1 | 9/2014 | White |
| 2014/0288480 A1 | 9/2014 | Zimmerman et al. |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0379076 A1 | 12/2014 | Vidlund et al. |
| 2015/0039081 A1 | 2/2015 | Costello |
| 2015/0045880 A1 | 2/2015 | Hacohen |
| 2015/0119978 A1 | 4/2015 | Tegels et al. |
| 2015/0142103 A1 | 5/2015 | Vidlund |
| 2015/0157457 A1 | 6/2015 | Hacohen |
| 2015/0173897 A1 | 6/2015 | Raanani et al. |
| 2015/0173898 A1 | 6/2015 | Drasler et al. |
| 2015/0196390 A1 | 7/2015 | Ma et al. |
| 2015/0216661 A1 | 8/2015 | Hacohen et al. |
| 2015/0257878 A1 | 9/2015 | Lane et al. |
| 2015/0265400 A1 | 9/2015 | Eidenschink et al. |
| 2015/0282922 A1 | 10/2015 | Hingston et al. |
| 2015/0282931 A1 | 10/2015 | Brunnett et al. |
| 2015/0313701 A1 | 11/2015 | Krahbichler |
| 2015/0335424 A1 | 11/2015 | McLean et al. |
| 2015/0351906 A1 | 12/2015 | Hammer et al. |
| 2015/0351910 A1 | 12/2015 | Gilmore et al. |
| 2016/0008131 A1 | 1/2016 | Christianson et al. |
| 2016/0038280 A1 | 2/2016 | Morriss et al. |
| 2016/0081799 A1 | 3/2016 | Leo et al. |
| 2016/0213470 A1 | 7/2016 | Ahlberg et al. |
| 2016/0213473 A1 | 7/2016 | Hacohen et al. |
| 2016/0220363 A1 | 8/2016 | Peter |
| 2016/0235525 A1 | 8/2016 | Rothstein et al. |
| 2016/0302921 A1 | 10/2016 | Gosal et al. |
| 2016/0310274 A1 | 10/2016 | Gross et al. |
| 2016/0324633 A1 | 11/2016 | Gross et al. |
| 2016/0324639 A1 | 11/2016 | Nguyen et al. |
| 2016/0367360 A1 | 12/2016 | Cartledge et al. |
| 2017/0020670 A1 | 1/2017 | Murray et al. |
| 2017/0035568 A1 | 2/2017 | Lombardi et al. |
| 2017/0056163 A1 | 3/2017 | Tayeb et al. |
| 2017/0056166 A1 | 3/2017 | Ratz et al. |
| 2017/0071733 A1 | 3/2017 | Ghione et al. |
| 2017/0071736 A1 | 3/2017 | Zhu et al. |
| 2017/0100236 A1 | 4/2017 | Robertson et al. |
| 2017/0128208 A1 | 5/2017 | Christianson et al. |
| 2017/0143446 A1 | 5/2017 | Kölbel |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181852 A1 | 6/2017 | Kassas |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0245993 A1 | 8/2017 | Gross et al. |
| 2017/0252163 A1 | 9/2017 | Kheradvar |
| 2017/0273784 A1 | 9/2017 | Racchini et al. |
| 2017/0281341 A1 | 10/2017 | Lim et al. |
| 2017/0319333 A1 | 11/2017 | Tegels et al. |
| 2017/0325943 A1 | 11/2017 | Robin et al. |
| 2017/0325948 A1 | 11/2017 | Wallace et al. |
| 2017/0333240 A1 | 11/2017 | Stangenes et al. |
| 2017/0348099 A1 | 12/2017 | Mendelson et al. |
| 2017/0360557 A1 | 12/2017 | Kheradvar et al. |
| 2017/0360558 A1 | 12/2017 | Ma |
| 2018/0000586 A1 | 1/2018 | Ganesan et al. |
| 2018/0014932 A1 | 1/2018 | Hammer et al. |
| 2018/0021130 A1 | 1/2018 | Danino |
| 2018/0042721 A1 | 2/2018 | Chambers |
| 2018/0098847 A1 | 4/2018 | Tuseth et al. |
| 2018/0116793 A1 | 5/2018 | Salahieh et al. |
| 2018/0147055 A1 | 5/2018 | Vidlund et al. |
| 2018/0153689 A1 | 6/2018 | Maimon et al. |
| 2018/0200049 A1 | 7/2018 | Chambers et al. |
| 2018/0206983 A1 | 7/2018 | Noe et al. |
| 2018/0256322 A1 | 9/2018 | Zhang et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0289474 A1 | 10/2018 | Rajagopal et al. |
| 2018/0289475 A1 | 10/2018 | Chung et al. |
| 2018/0296325 A1 | 10/2018 | McLean |
| 2018/0296341 A1 | 10/2018 | Noe et al. |
| 2018/0303612 A1 | 10/2018 | Pasquino et al. |
| 2018/0311037 A1 | 11/2018 | Morriss et al. |
| 2018/0318071 A1 | 11/2018 | Lozonschi et al. |
| 2018/0333259 A1 | 11/2018 | Dibie |
| 2018/0344456 A1 | 12/2018 | Barash et al. |
| 2018/0353293 A1 | 12/2018 | Colavito et al. |
| 2019/0000619 A1 | 1/2019 | Quijano et al. |
| 2019/0008636 A1 | 1/2019 | Francis et al. |
| 2019/0029819 A1 | 1/2019 | Huber |
| 2019/0060057 A1 | 2/2019 | Cohen et al. |
| 2019/0069995 A1 | 3/2019 | Levi et al. |
| 2019/0105153 A1 | 4/2019 | Barash et al. |
| 2019/0262129 A1 | 8/2019 | Cooper et al. |
| 2019/0321171 A1 | 10/2019 | Morriss et al. |
| 2019/0365538 A1 | 12/2019 | Chambers et al. |
| 2019/0388219 A1 | 12/2019 | Lane et al. |
| 2020/0008941 A1 | 1/2020 | Stappenbeck et al. |
| 2020/0093589 A1 | 3/2020 | Christianson et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |

(56) References Cited

U.S. PATENT DOCUMENTS

| | | |
|---|---|---|
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154010 A1 | 5/2021 | Schneider et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |
| 2021/0401572 A1 | 12/2021 | Nasr et al. |
| 2022/0000614 A1 | 1/2022 | Vidlund et al. |
| 2022/0087815 A1 | 3/2022 | Bernshtein et al. |
| 2022/0096226 A1 | 3/2022 | Christianson et al. |
| 2022/0160504 A1 | 5/2022 | Vidlund et al. |
| 2022/0249228 A1 | 8/2022 | Vidlund et al. |
| 2022/0280292 A1 | 9/2022 | Vidlund et al. |
| 2022/0280296 A1 | 9/2022 | Christianson et al. |
| 2022/0296369 A1 | 9/2022 | Kheradvar et al. |
| 2022/0323212 A1 | 10/2022 | Vidlund et al. |
| 2022/0338978 A1 | 10/2022 | Yushtein |
| 2022/0370198 A1 | 11/2022 | Nir et al. |
| 2022/0378410 A1 | 12/2022 | Hacohen et al. |
| 2022/0387174 A1 | 12/2022 | Schwarcz et al. |
| 2022/0395370 A1 | 12/2022 | Vidlund et al. |
| 2022/0409369 A1 | 12/2022 | Christianson et al. |
| 2023/0157816 A1 | 5/2023 | Perrin |
| 2023/0172710 A1 | 6/2023 | Nir |
| 2023/0190463 A1 | 6/2023 | Nir |
| 2023/0200990 A1 | 6/2023 | Chen et al. |
| 2023/0263630 A1 | 8/2023 | Saar et al. |
| 2023/0338140 A1 | 10/2023 | Cartledge et al. |
| 2024/0074855 A1 | 3/2024 | Atias et al. |
| 2024/0138983 A1 | 5/2024 | Ekvall et al. |
| 2024/0148497 A1 | 5/2024 | Bukin et al. |
| 2024/0225828 A1 | 7/2024 | Vidlund et al. |

FOREIGN PATENT DOCUMENTS

| | | |
|---|---|---|
| EP | 3897462 A1 | 10/2021 |
| JP | 2010508093 A | 3/2010 |
| JP | 2013517011 A | 5/2013 |
| JP | 2014528761 A | 10/2014 |
| JP | 2016508858 A | 3/2016 |
| JP | 2016533787 A | 11/2016 |
| JP | 2018515306 A | 6/2018 |
| WO | WO-2008055301 A1 | 5/2008 |
| WO | WO-2010079427 A1 | 7/2010 |
| WO | WO-2012035279 A1 | 3/2012 |
| WO | WO-2016183523 A1 | 11/2016 |
| WO | WO-2017123802 A1 | 7/2017 |
| WO | WO-2018136726 A1 | 7/2018 |
| WO | WO-2019195860 A2 | 10/2019 |
| WO | WO-2020061124 A1 | 3/2020 |
| WO | WO-2020061331 A2 | 3/2020 |
| WO | WO-2020131978 A1 | 6/2020 |
| WO | WO-2020146842 A1 | 7/2020 |
| WO | WO-2020154735 A1 | 7/2020 |
| WO | WO-2020181154 A2 | 9/2020 |
| WO | WO-2020186251 A1 | 9/2020 |
| WO | WO-2020227249 A1 | 11/2020 |
| WO | WO-2021035032 A1 | 2/2021 |
| WO | WO-2021040996 A1 | 3/2021 |
| WO | WO-2021146515 A1 | 7/2021 |
| WO | WO-2022010974 A1 | 1/2022 |
| WO | WO-2023164489 A2 | 8/2023 |
| WO | WO-2024081883 A1 | 4/2024 |
| WO | WO-2025006451 A1 | 1/2025 |

OTHER PUBLICATIONS

Office Action for Australian Application No. 2019342130 mailed May 22, 2024, 3 pages.
Office Action for Chinese Application No. 201980090378.6, with Search Report, mailed Mar. 12, 2024, 28 pages, English translation included.
Office Action for Chinese Application No. 202080074543.1, with Search Report, mailed Mar. 28, 2024, 18 pages, English translation included.
Office Action for Japanese Application No. 2021-516666 mailed Apr. 22, 2024, 6 pages, English translation included.
Office Action for Japanese Application No. 2021-535023 mailed Apr. 22, 2024, 4 pages, English translation included.
Office Action for Japanese Application No. 2021-547343 mailed May 13, 2024, 4 pages, English translation included.
Office Action for Japanese Application No. 2022-511360 mailed Apr. 18, 2024, 6 pages, English translation included.
Office Action for Japanese Application No. 2022-513172 mailed Apr. 18, 2024, 12 pages, English translation included.
Office Action for U.S. Appl. No. 17/707,493 mailed Jul. 8, 2024, 9 pages.
Office Action for U.S. Appl. No. 17/707,493 mailed Mar. 29, 2024, 21 pages.
Office Action for U.S. Appl. No. 18/410,230, mailed Jun. 4, 2024, 11 pages.
International Search Report and Written Opinion for International Application No. PCT/US2023/076845 dated Mar. 4, 2024, 10 pages.
Non-Final Office Action for U.S. Appl. No. 17/526,691 dated Mar. 11, 2024, 9 pages.
Office Action and Search report for Chinese Application No. CN201980075586.9 dated Feb. 5, 2024, 15 pages.
Office Action for Canadian Application No. CA3152042 dated Feb. 20, 2024, 5 pages.
Office Action for Canadian Patent Application No. CA20203152632 dated Feb. 19, 2024, 4 pages.
Office Action for Canadian Patent Application No. CA3113429 dated Feb. 13, 2024, 4 pages.
Office Action for Japanese Application No. JP20210563105 mailed Feb. 26, 2024, 8 pages.
Office Action for Japanese Patent Application No. JP20210555207 dated Jan. 31, 2024, 6 pages.
Office Action for Japanese Patent Application No. JP2021547343 dated Jan. 31, 2024, 6 pages.
Extended European Search Report for European Application No. 19863898.3, mailed Apr. 29, 2022, 13 pages.
Extended European Search Report for European Application No. 19897707.6, mailed Sep. 6, 2022, 7 pages.
Extended European Search Report for European Application No. 20745513.0, mailed Sep. 20, 2022, 9 pages.
Extended European Search Report for European Application No. 20767325.2, mailed on Oct. 25, 2022, 5 pages.
Extended European Search Report for European Application No. 20769769.9, mailed Oct. 17, 2022, 6 pages.
Extended European Search Report for European Application No. 20801681.6, mailed Jan. 18, 2023, 13 pages.
Extended European Search Report for European Application No. EP20854535 dated Jun. 23, 2023, 8 pages.
Extended European Search Report for European Application No. EP20856704 dated Aug. 22, 2023, 11 pages.
International Search Report and Written Opinion for International Application No. PCT/US2019/028822, mailed Oct. 24, 2019, 14 pages.
International Search Report and Written Opinion for International Application No. PCT/US2019/051615, mailed Mar. 2, 2020, 14 pages.

(56) References Cited

OTHER PUBLICATIONS

International Search Report and Written Opinion for International Application No. PCT/US2019/051957, mailed Apr. 30, 2020, 16 pages.
International Search Report and Written Opinion for International Application No. PCT/US2019/067010, mailed Mar. 10, 2020, 17 pages.
International Search Report and Written Opinion for International Application No. PCT/US2020/013240, mailed Jun. 3, 2020, 7 pages.
International Search Report and Written Opinion for International Application No. PCT/US2020/015231, mailed Apr. 23, 2020, 10 pages.
International Search Report and Written Opinion for International Application No. PCT/US2020/021300, mailed Oct. 7, 2020, 6 pages.
International Search Report and Written Opinion for International Application No. PCT/US2020/022828, mailed May 19, 2020, 12 pages.
International Search Report and Written Opinion for International Application No. PCT/US2020/031390, mailed Aug. 3, 2020, 10 pages.
International Search Report and Written Opinion for International Application No. PCT/US2020/045195, mailed Jan. 8, 2021, 18 pages.
International Search Report and Written Opinion for International Application No. PCT/US2020/047162, mailed Dec. 30, 2020, 9 pages.
International Search Report and Written Opinion for International Application No. PCT/US2021/013570, mailed Apr. 1, 2021, 9 pages.
International Search Report and Written Opinion for PCT Application No. PCT/US2023/063044 dated Oct. 24, 2023, 13 pages.
Invitation to pay additional fees for International Application No. PCT/US2023/063044, dated Jul. 31, 2023, 2 pages.
Office Action for European Application No. 19863898.3 mailed Nov. 27, 2023, 4 pages.
Office Action for European Application No. 20769769.9 dated Sep. 8, 2023, 4 pages.
Office Action for European Application No. EP20200801681 dated Dec. 11, 2023, 7 pages.
Office Action for European Application No. 19863898.3 dated Mar. 24, 2023, 6 pages.
Office Action for Japanese Application No. JP20210516666 dated Aug. 31, 2023, 19 pages.
Office Action for Japanese Application No. JP20210535023 dated Oct. 27, 2023, 17 pages.
Office Action for U.S. Appl. No. 16/155,890, mailed Feb. 8, 2019, 13 pages.
Office Action for U.S. Appl. No. 16/163,577, mailed Mar. 8, 2021, 10 pages.
Office Action for U.S. Appl. No. 16/435,687, mailed Aug. 7, 2019, 19 pages.
Office Action for U.S. Appl. No. 16/442,504, mailed Jan. 14, 2020, 11 pages.
Office Action for U.S. Appl. No. 16/443,862, mailed Nov. 12, 2021, 9 pages.
Office Action for U.S. Appl. No. 16/445,210, mailed Jan. 28, 2021, 7 pages.
Office Action for U.S. Appl. No. 16/448,108, mailed Jan. 21, 2020, 14 pages.
Office Action for U.S. Appl. No. 16/448,108, mailed Mar. 8, 2021, 8 pages.
Office Action for U.S. Appl. No. 16/448,108, mailed Sep. 1, 2020, 14 pages.
Office Action for U.S. Appl. No. 16/449,420, mailed Sep. 1, 2021, 16 pages.
Office Action for U.S. Appl. No. 16/455,417, mailed Sep. 23, 2019, 11 pages.
Office Action for U.S. Appl. No. 16/455,740, mailed Jul. 24, 2020, 7 pages.
Office Action for U.S. Appl. No. 16/711,415, mailed Jan. 18, 2022, 7 pages.
Office Action for U.S. Appl. No. 17/062,080, mailed Dec. 15, 2022, 14 pages.
Office Action for U.S. Appl. No. 17/154,227, mailed Jun. 18, 2021, 8 pages.
Office Action for U.S. Appl. No. 17/154,227, mailed Mar. 29, 2021, 6 pages.
Office Action for U.S. Appl. No. 17/154,438, mailed May 3, 2021, 16 pages.
Office Action for U.S. Appl. No. 17/167,983, mailed Apr. 13, 2021, 20 pages.
Office Action for U.S. Appl. No. 17/167,988, mailed Sep. 22, 2021, 19 pages.
Office Action for U.S. Appl. No. 17/193,936, mailed May 27, 2021, 6 pages.
Office Action for U.S. Appl. No. 17/207,076 dated Aug. 17, 2023, 6 pages.
Office Action for U.S. Appl. No. 17/221,547, mailed Aug. 4, 2021, 11 pages.
Office Action for U.S. Appl. No. 17/221,547, mailed Oct. 21, 2021, 9 pages.
Office Action for U.S. Appl. No. 17/222,182, mailed Sep. 2, 2021, 23 pages.
Office Action for U.S. Appl. No. 17/222,430, mailed Oct. 7, 2021, 17 pages.
Office Action for U.S. Appl. No. 17/236,219, mailed Aug. 4, 2021, 17 pages.
Office Action for U.S. Appl. No. 17/388,983, mailed Jan. 6, 2022, 11 pages.
Office Action for U.S. Appl. No. 17/666,086 dated Jul. 5, 2023, 16 pages.
International Search Report and Written Opinion for International Application No. PCT/US2024/035388, mailed Dec. 3, 2024, 12 pages.
Invitation to Pay Additional Fees for International Application No. PCT/US2024/035388, mailed Sep. 17, 2024, 3 pages.
Office Action for Australian Application No. 2019406832 mailed Jul. 26, 2024, 4 pages.
Office Action for Australian Application No. 2020231221 mailed Sep. 11, 2024, 4 pages.
Office Action for Australian Application No. 2020239265 mailed Sep. 2, 2024, 3 pages.
Office Action for European Application No. 20801681.6 mailed Jul. 31, 2024, 5 pages.
Office Action for European Application No. 20856704.0 mailed Jul. 29, 2024, 4 pages.
Office Action for U.S. Appl. No. 17/372,022 mailed Aug. 1, 2024, 15 pages.
Office Action for U.S. Appl. No. 17/682,875, mailed Sep. 28, 2024, 18 pages.
Office Action for U.S. Appl. No. 17/825,551, mailed Aug. 29, 2024, 11 pages.
Office Action for U.S. Appl. No. 18/410,230, mailed Nov. 5, 2024, 6 pages.

Expanded orthogonal valve

Single tether cinch

Double tether cinch

Double tether on septal side

Single tether on septal wall

Cinched $R_1 = D_L - 2x$ $r_1 = D_W - y$

Expanded

Double-wall cinch-septal and ant-pos walls

Expanded

Cinched

FIG. 34
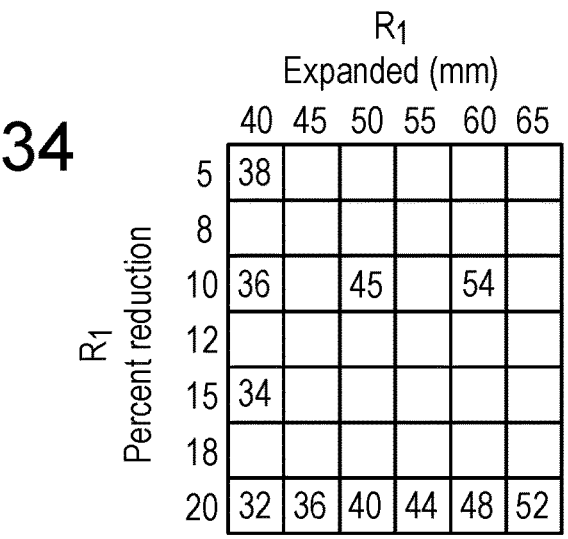
FIG. 35
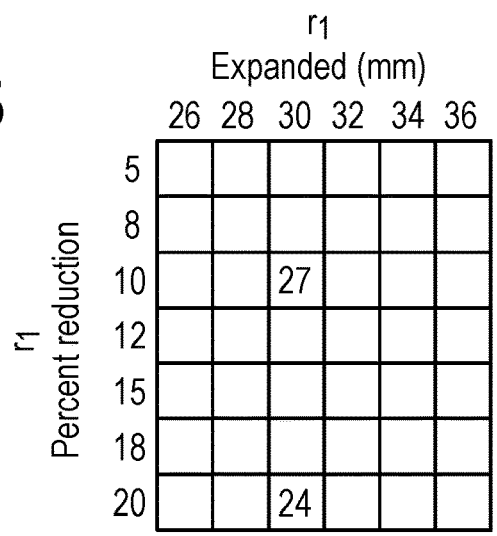
FIG. 36
Perimeter of ellipse  $p \approx \pi [\, 3(a+b) - \sqrt{(3a+b)(a+3b)}\, ]$ (Ramanujan)
$a = R_{1/2}$
$b = r_{1/2}$
| Example | | | |
|---|---|---|---|
| Expanded valve | 60 mm (d) a=30 | 30 mm (w) b=15 | $C \approx 145.33$ mm |
| 10% Cinched valve | 54 | 27 | $C \approx 138$ mm |
| 20% Cinched valve | 48 | 24 | $C \approx 116.26$ mm |

FIG. 38A
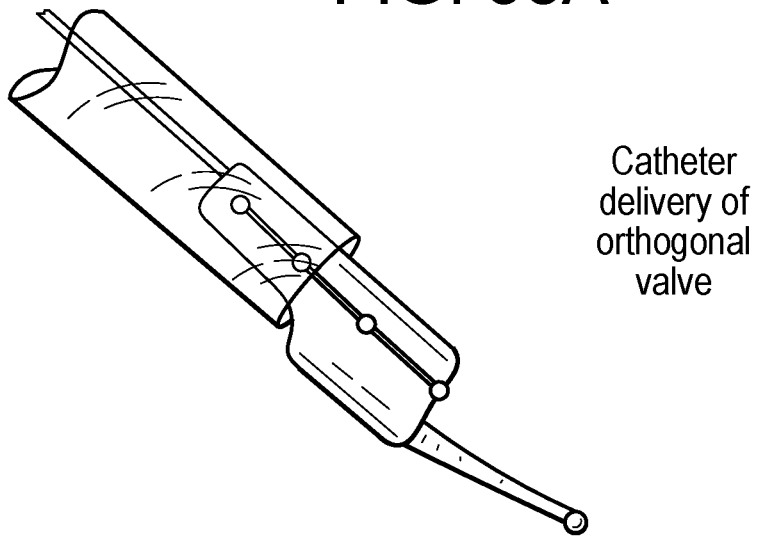
Catheter delivery of orthogonal valve
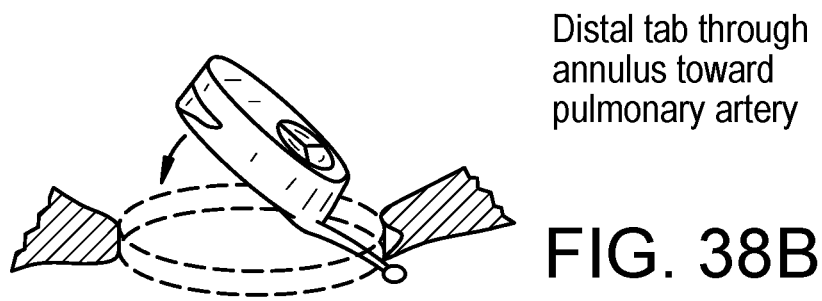
Distal tab through annulus toward pulmonary artery
FIG. 38B
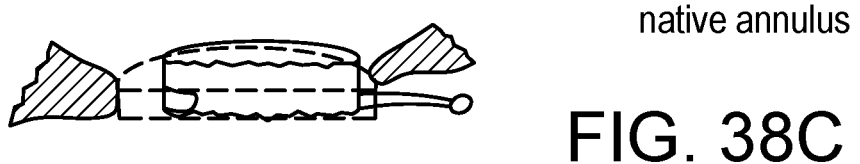
Seat valve into native annulus
FIG. 38C
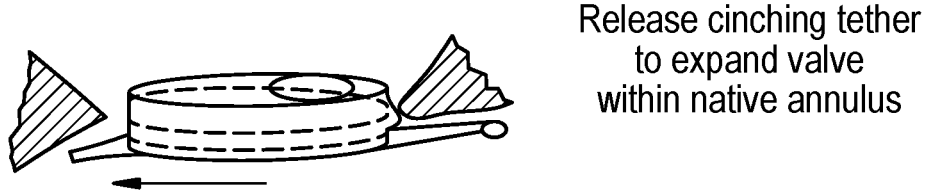
Release cinching tether to expand valve within native annulus
FIG. 38D

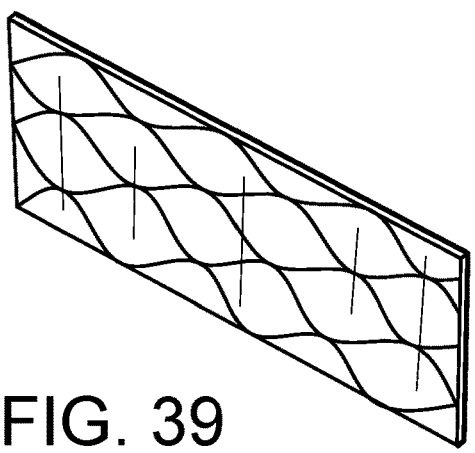
FIG. 39
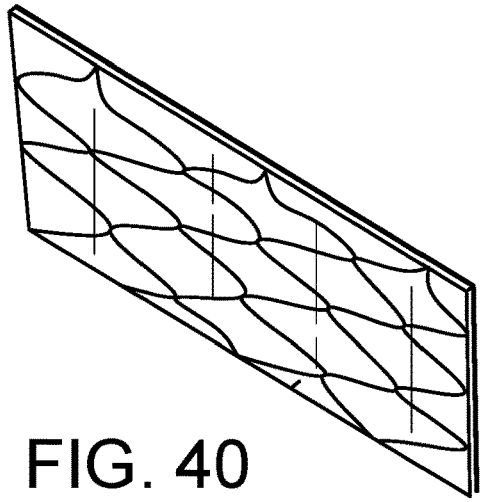
FIG. 40
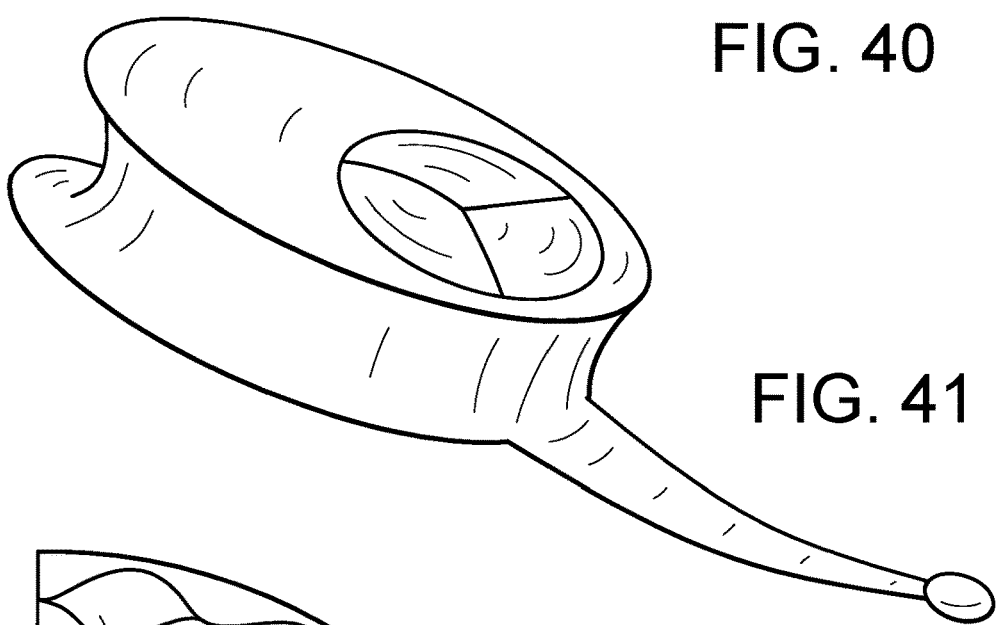
FIG. 41
FIG. 42
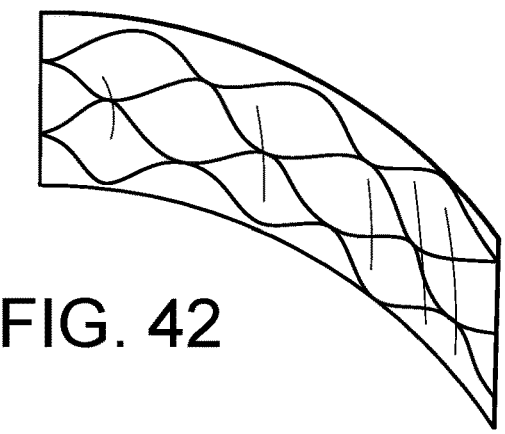
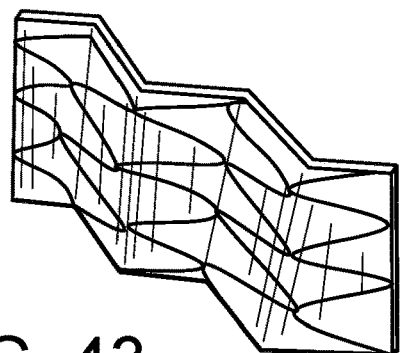
FIG. 43

CINCH DEVICE AND METHOD FOR DEPLOYMENT OF A SIDE-DELIVERED PROSTHETIC HEART VALVE IN A NATIVE ANNULUS

CROSS-REFERENCE TO RELATED APPLICATIONS

This application is a continuation of U.S. patent application Ser. No. 17/550,400, filed Dec. 14, 2021, entitled "Cinch Device and Method for Deployment of a Side-Delivered Prosthetic Heart Valve in a Native Annulus," now U.S. Pat. No. 11,712,335, which is a divisional of U.S. patent application Ser. No. 17/236,219, filed Apr. 21, 2021, entitled "Cinch Device and Method for Deployment of a Side-Delivered Prosthetic Heart Valve in a Native Annulus," now U.S. Pat. No. 11,202,706, which is a continuation of International Patent Application No. PCT/US2020/031390, filed May 4, 2020, entitled "Cinch Device and Method for Deployment of a Side-Delivered Prosthetic Heart Valve in a Native Annulus," which claims priority to and the benefit of U.S. Provisional Application No. 62/843,424, filed May 4, 2019, entitled "Cinch Device and Method for Deployment of Orthogonal Prosthetic Heart Valve in a Native Annulus," the disclosure of each of which is incorporated herein by reference in its entirety.

BACKGROUND

Embodiments are described herein that relate to prosthetic heart valves, and in particular to a cinch device and method for deployment of an orthogonal prosthetic heart valve in a native annulus.

Prosthetic heart valves can pose challenges for delivery and deployment within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to the lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space).

Accordingly, a need exists for prosthetic valves with one or more deployment-assistive features while maintaining a relatively small, compressed size that allows for transcatheter delivery of the valve.

SUMMARY

The present invention is directed to a cinching apparatus to reduce the circumference of the trans-annular sidewall of a valve during deployment, followed by release of the cinching apparatus to expand the circumference to full size and obtain a secure sealing of the native annulus for a transcatheter heart valve replacement, the valve having a proximal sub-annular anchoring tab and a distal sub-annular anchoring tab, and in particular a side-delivered (length-wise) transcatheter prosthetic heart valve having a annular support frame having compressible wire cells that facilitate rolling, folding, compressing in height and/or width, the valve length-wise, or orthogonal, to the central axis of the flow control component, allowing a very large diameter valve to be delivered and deployed from the inferior vena cava directly into the tricuspid valve, e.g., has a height of about 5-60 mm and a diameter of about 25-80 mm, without requiring an oversized diameter catheter and without requiring delivery and deployment from a catheter at an acute angle of approach.

BRIEF DESCRIPTION OF THE DRAWINGS

FIG. 34 is a chart showing the percentage reduction of the long-axis R1 of the ellipse of the valve and the calculated shrinkage of the circumference.

FIG. 35 is a chart showing the percentage reduction of the short-axis r1 of the ellipse of the valve and the calculated shrinkage of the circumference.

FIG. 36 is a chart showing the percentage reduction of the long-axis R1 of the ellipse of the valve and the calculated shrinkage of the circumference.

FIGS. 38A to 38D illustrate a valve delivery catheter working in conjunction with a cinching apparatus catheter to deliver the valve to the native annulus, and then to release/uncinch the valve to effectuate a good seal simultaneous with more predictable seating of the valve in the annulus.

FIG. 39 is an illustration of one type of wire frame panel showing a wire frame configuration that is balanced between horizontal compression and lateral compression.

FIG. 40 is an illustration of one type of wire frame panel showing a wire frame configuration that is weighted more towards horizontal compression than lateral compression.

FIG. 41 is an illustration of a percutaneously delivered prosthetic tricuspid valve via the femoral-vein.

FIG. 42 is an illustration of one type of wire frame panel showing a wire frame configuration that is weighted more towards horizontal compression than lateral compression.

FIG. 43 is an illustration of one type of wire frame panel showing a wire frame configuration that is balanced between horizontal compression and lateral compression.

DETAILED DESCRIPTION OF THE INVENTION

Figure 1:
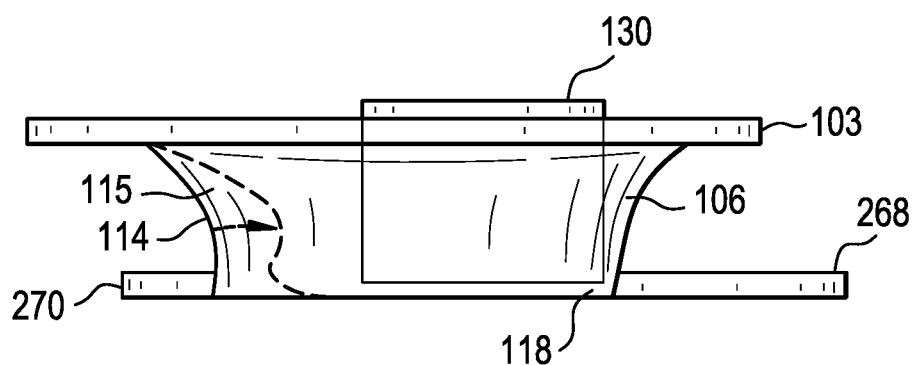
FIG. 1 is a schematic cross-sectional side view according to an embodiment.

The invention is directed to cinching apparatus for reducing the size, distal to proximal, of the valve to facilitate deployment of the large orthogonal valve into the native annulus, and then to release the cinched configuration and allow the valve to expand once positioned within the annulus to effectuate a secure sealing for a dual-tab transcatheter heart valve replacement that is a low profile, orthogonally delivered implantable prosthetic heart valve having an ring-shaped or annular support frame, an inner 2- or 3-panel sleeve, an elongated sub-annular distal anchoring tab extending into the right ventricular outflow tract, an elongated sub-annular proximal anchoring tab extending into the proximal sub-annular space, preferably between the anterior and the posterior leaflets.

In some implementations, the embodiments described herein are directed a side-delivered transcatheter prosthetic heart valve having an integrated cinching apparatus, comprising: (a) a self-expanding annular support frame, said annular support frame having a central channel and an outer perimeter wall circumscribing a central vertical axis in an expanded configuration, an atrial sealing collar is disposed around at least a portion of a top edge of the outer perimeter wall, said annular support frame having a distal side and a proximal side; (b) an integrated cinching apparatus comprising an elongated tether or strap attached to the annular support frame, the tether or strap actuated from a control handle of a steerable catheter to cinch or reduce the radial size of the proximal side of the annular support frame; (c) a flow control component mounted within the annular support frame and configured to permit blood flow in a first direction through an inflow end of the valve and block blood flow in a second direction, opposite the first direction, through an outflow end of the valve; (d) a subannular distal anchoring tab or tension arm is attached to a distal portion of the perimeter wall and extending away from the perimeter wall 10-40 mm; (e) a sub annular proximal anchoring tab or tension arm attached to a proximal portion of the perimeter wall and extending away from the perimeter wall 5-20 mm; wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis; wherein the horizontal axis of the compressed configuration of the valve is substantially parallel to a length-wise cylindrical axis of the delivery catheter; wherein the valve has a height of about 5-60 mm and a diameter of about 25-80 mm.

Any of the prosthetic heart valves described herein can include an integrated cinching apparatus that has two (2) or more tethers.

Any of the prosthetic heart valves described herein can include wherein the integrated cinching apparatus comprises a single-pull tether mechanism, a double tether pulling system, a multiple tether twisting mechanism, or a belt cinching mechanism.

Any of the prosthetic heart valves described herein can include wherein the tether is braided polyethylene, treated pericardial tissue, ePTFE, or nitinol.

Any of the prosthetic heart valves described herein can include wherein the tether or strap has a tooth-portion and the releasing element has tooth-engaging releasable pawl element.

Any of the prosthetic heart valves described herein can include wherein the first tether or strap is attached to a top portion of a septal side of the perimeter wall, and the second tether or strap is attached to a bottom portion of the septal side of the perimeter wall.

Any of the prosthetic heart valves described herein can include wherein the tether or strap is releasably attached to the subannular proximal anchoring tab, and the proximal anchoring tab is configured to move from a folded up position against the perimeter wall to an expanded position folding away from the perimeter wall, wherein the proximal anchoring tab has a tab anchoring element, and the tether or strap has a tab releasing element that cooperates with the tab anchoring element to move the proximal anchoring tab from the folded up position to the expanded position.

Any of the prosthetic heart valves described herein can include wherein the annular support frame is covered with a biocompatible material.

Any of the prosthetic heart valves described herein can include wherein the annular support frame is comprised of a plurality of compressible wire cells having an orientation and cell geometry substantially orthogonal to the central vertical axis to minimize wire cell strain when the annular support frame is configured in a vertical compressed configuration, a rolled compressed configuration, or a folded compressed configuration.

Any of the prosthetic heart valves described herein can include wherein the annular support frame has a lower body portion and an upper collar portion, wherein the lower body portion in an expanded configuration forms a shape selected from a funnel, cylinder, flat cone, or circular hyperboloid Any of the prosthetic heart valves described herein can include wherein said annular support frame is comprised of a braided, wire, or laser-cut wire frame, and said annular support frame is covered with a biocompatible material.

Any of the prosthetic heart valves described herein can include wherein the annular support frame has a side profile of a flat cone shape having a diameter R of 40-80 mm, a diameter r of 20-60 mm, and a height of 5-60 mm.

Any of the prosthetic heart valves described herein can include wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

Any of the prosthetic heart valves described herein can include wherein the annular support frame has a side profile of an hourglass shape having a top diameter R1 of 40-80 mm, a bottom diameter R2 of 50-70 mm, an internal diameter r of 20-60 mm, and a height of 5-60 mm.

Any of the prosthetic heart valves described herein can include wherein the valve in an expanded configuration has a central vertical axis that is substantially parallel to the first direction.

Any of the prosthetic heart valves described herein can include wherein the flow control component has an internal diameter of 20-40 mm, and a plurality of leaflets of pericardial material joined to form a rounded cylinder at an inflow end and having a flat closable aperture at an outflow end.

Any of the prosthetic heart valves described herein can include wherein the flow control component is supported with one or more longitudinal supports integrated into or mounted upon the flow control component, the one or more longitudinal supports selected from rigid or semirigid posts, rigid or semi-rigid ribs, rigid or semi-rigid battens, rigid or semi-rigid panels, and combinations thereof.

Any of the prosthetic heart valves described herein can include wherein the subannular distal anchoring tab is comprised of wire loop, a wire frame, a laser cut frame, an integrated frame section, or a stent, and the distal anchoring tab extends from about 20-40 mm away from the distal side of the annular support frame.

Any of the prosthetic heart valves described herein can include wherein the proximal anchoring tab is comprised of wire loop, a wire frame, a laser cut frame, an integrated frame section, or a stent, and the proximal anchoring tab extends from about 10-20 mm away from the proximal side of the annular support frame.

Any of the prosthetic heart valves described herein can include an upper distal anchoring tab attached to a distal upper edge of the annular support frame, the upper distal anchoring tab comprised of wire loop, a wire frame, a laser cut frame, an integrated frame section, or a stent, and extends from about 10-20 mm away from the annular support frame.

Any of the prosthetic heart valves described herein can include wherein at least one tissue anchor connected to the annular support frame for engaging native tissue.

Any of the prosthetic heart valves described herein can include wherein the outer perimeter wall comprises a front wall portion that is a first flat panel and a back wall portion that is a second flat panel, and wherein a proximal fold area and a distal fold area each comprise a sewn seam, a fabric panel, a rigid hinge, or a flexible fabric span without any wire cells.

Any of the prosthetic heart valves described herein can include wherein the annular support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

Any of the prosthetic heart valves described herein can include wherein the invention provides a process for manufacturing an orthogonally delivered transcatheter prosthetic heart valve frame, comprising: using additive or subtractive metal or metal-alloy manufacturing to produce a self-expanding annular support frame, said annular support frame having a central channel and an outer perimeter wall circumscribing a central vertical axis in an expanded configuration, an atrial sealing collar is disposed around at least a portion of a top edge of the outer perimeter wall, said annular support frame having a distal side and a proximal side, an integrated cinching apparatus, a flow control component mounted within the annular support frame and configured to permit blood flow in a first direction through an inflow end of the valve and block blood flow in a second direction, opposite the first direction, through an outflow end of the valve, an integrated subannular anchor system attached to the annular support frame, the anchor system comprising an elongated tether or strap attached at a distal end to a rigid loop, and a slidable locking element slidably attached to the elongated tether or strap, a distal anchoring tab mounted on the distal side of the annular support frame, a proximal anchoring tab mounted on the proximal side of the annular support frame, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a length-wise cylindrical axis of the delivery catheter, wherein the valve has a height of about 5-60 mm and a diameter of about 25-80 mm, wherein the additive metal or metal-alloy manufacturing is 3D printing or direct metal laser sintering (powder melt), and wherein the subtractive metal or metal-alloy manufacturing is photolithography, laser sintering/cutting, cnc machining, electrical discharge machining.

Any of the prosthetic heart valves described herein can include further steps of: (ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Any of the method for compressing an implantable prosthetic heart valve for length-wise orthogonal release of the valve from a delivery catheter, can include the steps: flattening, rolling or folding the implantable prosthetic heart valve into a compressed configuration wherein the long-axis of the compressed configuration of the valve is substantially parallel to a length-wise cylindrical axis of the delivery catheter, wherein the implantable prosthetic heart valve comprises an annular support frame having a flow control component mounted within the annular support frame and configured to permit blood flow in a first direction through an inflow end of the valve and block blood flow in a second direction, opposite the first direction, through an outflow end of the valve, an integrated cinching system attached to the annular support frame, a distal anchoring tab mounted on a distal side of the annular support frame, a proximal anchoring tab mounted on a proximal side of the annular support frame, wherein the valve has a height of about 5-60 mm and a diameter of about 25-80 mm.

In another preferred embodiment, wherein the implantable prosthetic heart valve is rolled or folded into a compressed configuration using a step selected from the group consisting of: unilaterally rolling into a compressed configuration from one side of the annular support frame; bilaterally rolling into a compressed configuration from two opposing sides of the annular support frame; flattening the annular support frame into two parallel panels that are substantially parallel to the long-axis, and then rolling the flattened annular support frame into a compressed configuration; and flattening the annular support frame along a vertical axis to reduce a vertical dimension of the valve from top to bottom.

In another preferred embodiment, method for orthogonal delivery of implantable prosthetic heart valve to a desired location in the body, the method can comprise the step: advancing a delivery catheter to the desired location in the body and delivering an expandable prosthetic heart valve to the desired location in the body by releasing the valve from the delivery catheter, wherein the valve comprises a self-expanding annular support frame, said annular support frame having a central channel and an outer perimeter wall circumscribing a central vertical axis in an expanded configuration, an atrial sealing collar is disposed around at least a portion of a top edge of the outer perimeter wall, said annular support frame having a distal side and a proximal side, an integrated cinching apparatus; a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, and a proximal anchoring tab mounted on a proximal side of the annular support frame, wherein said valve is cinchable to a cinched configuration having an elliptical circumference from 5-30% reduced from an expanded configuration, or having a cinched configuration where a long-axis of the top edge is reduced 5-30% in diameter, wherein the valve is compressible to a compressed configuration having a height of 5-10 mm and a width of 5-10 mm for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush Groups, those skilled in the art will recognize that the disclosure is also thereby described in terms of any individual member or subgroup of members of the Markush Group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Integrated Cinching Apparatus

In the description and claims herein, the term "integrated cinching apparatus," "cinch," is used to describe an elongated tether that is attached to the frame of the valve in such a way that pulling on the tether will fold/bunch/curve the perimeter wall of the annular support frame thus reducing the circumference of the entire valve, making it easier to deploy the valve into the native annulus. The tether is attached to (exterior) or extends through (interior) the body/perimeter wall and/or collar portion of the prosthetic valve. The cinch apparatus may have, in a preferred embodiment, a radio-opaque marker or radio-opaque material or structure so that a delivery system catheter can be guided through the body of a patient to the site where the valve is mounted or to be mounted. In one preferred embodiment, delivery of an orthogonal valve is (length-wise delivery, height- and width-compression) through the femoral vein to the inferior vena cava (IVC) to the right atrium of the heart for anchoring the prosthetic tricuspid heart valve replacement, followed by IVC delivery of the anchoring system to install the subannular anchors.

Side-Delivered, Side-Delivery, or Orthogonal

In the description and claims herein, the terms "side-delivered," "side-delivery," or "orthogonal" are used to describe that the valves of the present invention are compressed and delivered at a roughly 90 degree angle compared to traditional transcatheter heart valves. Traditional valves have a central cylinder axis that is parallel to the length-wise axis of the delivery catheter and are deployed from the end of the delivery catheter in a manner akin to pushing a closed umbrella out of a sleeve. The valves of the present invention are compressed and delivered in a sideways manner. Traditional valves can only be expanded as large as what the internal diameter of the delivery catheter will allow. Efforts to increase the expanded diameter of traditional valves have run into the problems of trying to compress too much material and structure into too little space. Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, e.g., from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In preferred embodiments of the invention, the transcatheter approach includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g., Fossa ovalis or lower, via the IVC-femoral or the SVC jugular approach.

Annular Support Frame

In the description and claims herein, the term "annular support frame," and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular support frame has a flow control component mounted within the annular support frame and configured to permit blood flow in a first direction through an inflow end of the valve and block blood flow in a second direction, opposite the first direction, through an outflow end of the valve.

Since the frame is preferably made of superelastic metal or alloy such as nitinol, the frame is compressible. Preferably, the frame is constructed of a plurality of compressible wire cells having an orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In one preferred embodiment, the annular support frame used in the prosthetic heart valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, which is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut nitinol tube, or flat sheet or other similarly functioning material such as braided wire.

The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, nitinol has been found to be especially useful since it can be processed to be austenitic, martensitic or super elastic. Martensitic and super elastic alloys can be processed to demonstrate the required mechanical behavior.

Annular Frame Anchor Elements

The cinching tether releasably attaches to the valve, and includes a variety of mechanisms for how the tether is actuated. In one embodiment, the end of the tether has a release device, and the remainder of the tether is threaded through guide holes or tubes mounted on the frame. In another embodiment, the tether is attached to multiple locations in order to folded one or both sides of the valve (perimeter wall), either in one large bend, or in multiple smaller bends. In another embodiment, there can be more than one tether. For example, in one embodiment, there might be two tethers on one side of the valve, only reducing one side. In another embodiment, there might a tethers on opposing sides of valve, e.g., septal and anterior, to shrink or collapse the circumference of the valve.

Laser Cut

One possible construction of the wire frame envisions the laser cutting of a thin, isodiametric nitinol tube. The laser cuts form regular cutouts in the thin nitinol tube. In one preferred embodiment, the nitinol tube expands to form a three-dimensional structure formed from diamond-shaped cells. The structure may also have additional functional elements, e.g., loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a nitinol wire and a simple braiding fixture. The wire is wound on the braiding fixture in a pattern until an isodiametric tube is formed. Secondarily, the braided wire frame is placed on a shaping fixture and processed using industry standard nitinol shape forming methods.

Flow Control Component

In the description and claims herein, the term "flow control component" refers in a nonlimiting sense to a leaflet structure having 2-, 3-, 4-leaflets of flexible biocompatible material such a treated or untreated pericardium that is sewn or joined to an annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated in a valve-in-valve embodiment to also include a wide variety of (bio)prosthetic artificial heart valves, including ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

Transcatheter

The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Transcatheter can be synonymous with transluminal and is functionally related to the term "percutaneous" as it relates to delivery of heart valves. As used herein, the term "lumen" can refer to the inside of a cylinder or tube. The term "bore" can refer to the inner diameter of the lumen.

Tissue Anchor

In the description and claims herein, the term "tissue anchor" or "plication tissue anchor" or "secondary tissue anchor," or "dart" or "pin" refers to a fastening device that connects the upper atrial frame to the native annular tissue, usually at or near the periphery of the collar. The anchor may be positioned to avoid piercing tissue and just rely on the compressive force of the two platelike collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK that may be mounted on a spoked frame and that runs axially, or down the center of, or within a sewn seam of, the flexible sleeve.

The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—the volume of fluid displaced by one complete stroke or revolution.

Ejection fraction is a measurement of the percentage of blood leaving your heart each time it contracts. During each heartbeat pumping cycle, the heart contracts and relaxes. When your heart contracts, it ejects blood from the two pumping chambers (ventricles).

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "nonexpandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g., a new mechanical valve replaces a native valve, as well as medical devices that take the place of and/or assist, repair, or improve existing anatomical parts, e.g., native valve is left in place. For mounting within a passive assist cage, the invention contemplates a wide variety of (bio)prosthetic artificial heart valves. Contemplated as within the scope of the invention are ball valves (e.g., Starr-Edwards), bileaflet valves (St. Jude), tilting disc valves (e.g., Bjork-Shiley), stented pericardium heart-valve prosthesis (bovine, porcine, ovine) (Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers

The tethers are made from surgical-grade materials such as biocompatible polymer suture material. Non-limiting examples of such material include ultra-high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Polymers

In some embodiments, components may be fabricated from a synthetic material(s) such a polyurethane or polytetrafluoroethylene (PTFE). Where a thin, durable synthetic material is contemplated (e.g., for a covering) synthetic polymer materials such expanded PTFE or polyester may optionally be used. Other suitable materials may optionally include thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene, high-density polyethylene, and ultra-high molecular weight polyethylene. Additional biocompatible polymers may optionally include elastomers, polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron®), Poly-L-lactic acids (PLLA), polyglycolic acid (PGA), poly(D, L-lactide/glycolide) copolymer (PDLA), silicone polyesters, polyamides (nylon), PTFE, elongated PTFE, expanded PTFE, polyurethanes, siloxane polymers and/or oligomers, and/or polylactones, and block co-polymers using the same.

Components

In some embodiments, a valve frame and/or components thereof may be fabricated from biocompatible metals, metal alloys, polymer coated metals, and/or the like. Suitable biocompatible metals and/or metal alloys can include stainless steel (e.g., 316L stainless steel), cobalt chromium (Co—Cr) alloys, nickel-titanium alloys (e.g., Nitinol®), and/or the like. Suitable polymer coatings can include polyethylene vinyl acetate (PEVA), poly-butyl methacrylate (PBMA), translute styrene isoprene butadiene (SIBs) copolymer, polylactic acid, polyester, polylactide, D-lactic polylactic acid (DLPLA), and/or the like.

Covering

Any of the valve frames and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old.

Covered Wire Frame Materials

Drug-eluting wire frames are contemplated for use herein. Des basically consist of three parts: wire frame platform, coating, and drug. Some of the examples for polymer free des are amazon pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316L stainless steel wire frame as base for the drug Tacrolimus and utilizing integrated turbostratic carbofilm as the drug carrier. VESTA sync (MIV Therapeutics) using GenX stainless steel (316L) as base utilizing microporous hydroxyapatite coating as carrier for the drug Sirolimus. YUKON choice (Translumina) used 316L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316L stainless steel coated with polyethylene vinyl acetate (PEVA) and poly-butyl methacrylate (PBMA) for carrying the drug Sirolimus. Taxus (Boston Scientific) utilizes 316L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying Zotarolimus with phosphorylcholine as drug carrier. BioMatrix employing S-Wire frame (316L) stainless steel as base with polylactic acid surface for carrying the antiproliferative drug Biolimus. ELIXIR-DES program (Elixir Medical Corp) consisting both polyester and polylactide coated wire frames for carrying the drug Novolimus with cobalt-chromium (Co—Cr) as base. JACTAX (Boston Scientific Corp.) utilized D-lactic polylactic acid (DLPLA) coated (316L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Example

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In a preferred embodiment the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example—Delivery Process

Orthogonal delivery steps: provide a foldable, compressible prosthetic tricuspid valve, load the valve sideways into a delivery catheter, advance the valve to the heart via the IVC or the SVC over a pre-placed guidewire that is threaded onto a guidewire loop of a subannular distal tab, partially expel the valve to position the distal subannular tab, to wedge the channel of the valve body against the distal annular ring, with the atrial collar disposed on a top surface of the annular tissue region, and to allow the valve leaflets to begin functioning use a cinching system to radially reduce the proximal side of the valve body, complete deployment of the valve by seating into the native annulus, and extend/unfold subannular proximal anchoring tab.

Example—Manufacturing Process

In a preferred embodiment the invention includes a process for manufacturing an orthogonally delivered transcatheter prosthetic heart valve frame, comprising: (i) using additive or subtractive metal or metal-alloy manufacturing to produce a self-expanding annular support frame, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining.

In another preferred embodiment, there is provided a process for manufacturing an orthogonally delivered transcatheter prosthetic heart valve frame, further comprising the steps of: (ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Example—Compression Methods

In another preferred embodiment, there is provided a method of compressing, wherein the implantable prosthetic heart valve is rolled or folded into a compressed configuration using a step selected from the group consisting of: (i) unilaterally rolling into a compressed configuration from one side of the annular support frame; (i) bilaterally rolling into a compressed configuration from two opposing sides of the annular support frame; (iii) flattening the annular support frame into two parallel panels that are substantially parallel to the long-axis, and then rolling the flattened annular support frame into a compressed configuration; and (iv) flattening the annular support frame along a vertical axis to reduce a vertical dimension of the valve from top to bottom.

DRAWINGS

Referring now to the drawings, FIG. 1 is a schematic cross-sectional side view according to an embodiment. FIG. 1 shows how the perimeter (circumference) of the lower transannular portion 106 of the valve 100 can be cinched inward. This allows the valve to be designed with an over-sized transannular circumference, e.g., 5-20%, often 10-15%, to promote a tight fit of the valve within the native annulus and provide a good seal against perivalvular leakage (PVLs). The cinching process pulls the proximal sidewall inwards and reduces the circumference of the transannular section 106. This allows the oversized valve to drop into the native annulus during deployment of the valve. Then, once the valve is seated as desired, the transannular section is pushed back out to its full or nearly full, circumference, and thereby form a tight, sealed fit of the prosthetic valve in the native annulus.

Figure 2:
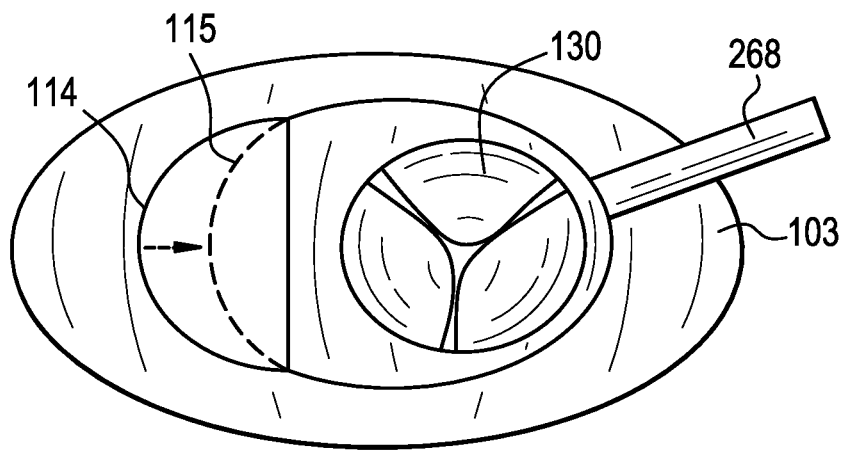
FIG. 2 is a schematic bottom view according to an embodiment.

FIG. 2 is a schematic bottom view according to an embodiment. FIG. 2 shows a view from below and shows how the perimeter (circumference) of the lower transannular portion of the valve can be cinched inward, here the proximal end of the transannular section of the valve. This over-sized transannular circumference, e.g., 5-20%, often 10-15%, promotes a tight fit of the valve within the native annulus and provides a good seal against perivalvular leakage (PVLs).

Figure 3:
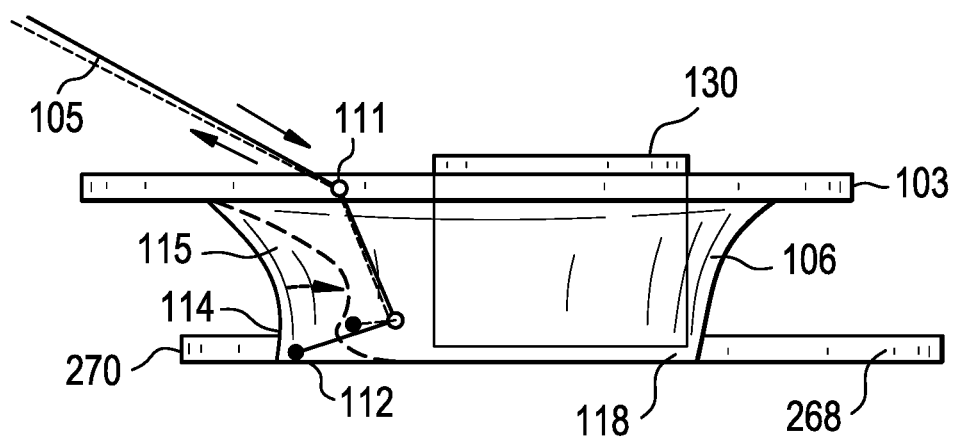
FIG. 3 is an image of one embodiment of the present invention, with cinching assembly attached to the orthogonally deliverable valve.

FIG. 3 is a schematic cross-sectional side view according to a proximal tether embodiment. FIG. 3 shows how the perimeter (circumference) of the lower transannular portion 106 of the valve 100 can be cinched inward. This allows the valve to be designed with an over-sized transannular circumference, e.g., 5-20%, often 10-15%, to promote a tight fit of the valve within the native annulus and provide a good seal against perivalvular leakage (PVLs). Proximal end cinch tether 105 shows a non-limiting mechanism for performing the cinching process. Cinch tether 105 travels from a delivery catheter (not shown) through way-guide components such a eyelets 111. In this embodiment, the cinch tether 105 travels through the collar 103 by way of the eyelets to the cinch tether mount on the proximal side 114 of the transannular section 106 of the lower part of the valve 100. Pulling the cinch tether proximally, towards the operator, pulls the proximal sidewall inwards and reduces the circumference of the transannular section 106. This allows the oversized valve to drop into the native annulus during deployment of the valve. Then, once the valve is seated as desired, the cinch tether 105 can be advanced (or released if the transannular section is spring-biased into the folded configuration) to push the proximal side 114 back out to its full or nearly full, circumference, and thereby form a tight, sealed fit of the prosthetic valve in the native annulus.

Figure 4:
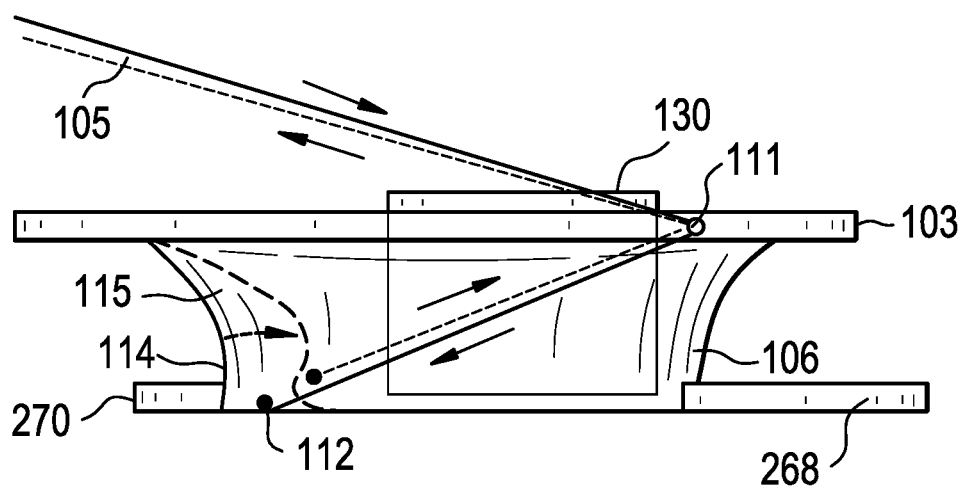
FIG. 4 is a schematic cross-sectional side view according to a distal end tether assembly embodiment.

FIG. 4 is a schematic cross-sectional side view according to a distal tether embodiment. FIG. 4 shows how the perimeter (circumference) of the lower transannular portion 106 of the valve 100 can be cinched inward. This allows the valve to be designed with an over-sized transannular circumference, e.g., 5-20%, often 10-15%, to promote a tight fit of the valve within the native annulus and provide a good seal against perivalvular leakage (PVLs). Distal end cinch tether 105 shows a non-limiting mechanism for performing the cinching process. Cinch tether 105 travels from a delivery catheter (not shown) through way-guide components such a eyelets 111. In this embodiment, the cinch tether 105 travels through the collar 103 by way of the eyelets to the cinch tether mount on the proximal side 114 of the transannular section 106 of the lower part of the valve 100. Pulling the cinch tether proximally, towards the operator, pulls the proximal sidewall inwards and reduces the circumference of the transannular section 106. This allows the oversized valve to drop into the native annulus during deployment of the valve. Then, once the valve is seated as desired, the cinch tether 105 can be advanced (or released if the transannular section is spring-biased into the folded configuration) to push the proximal side 114 back out to its full or nearly full, circumference, and thereby form a tight, sealed fit of the prosthetic valve in the native annulus.

Figure 5:
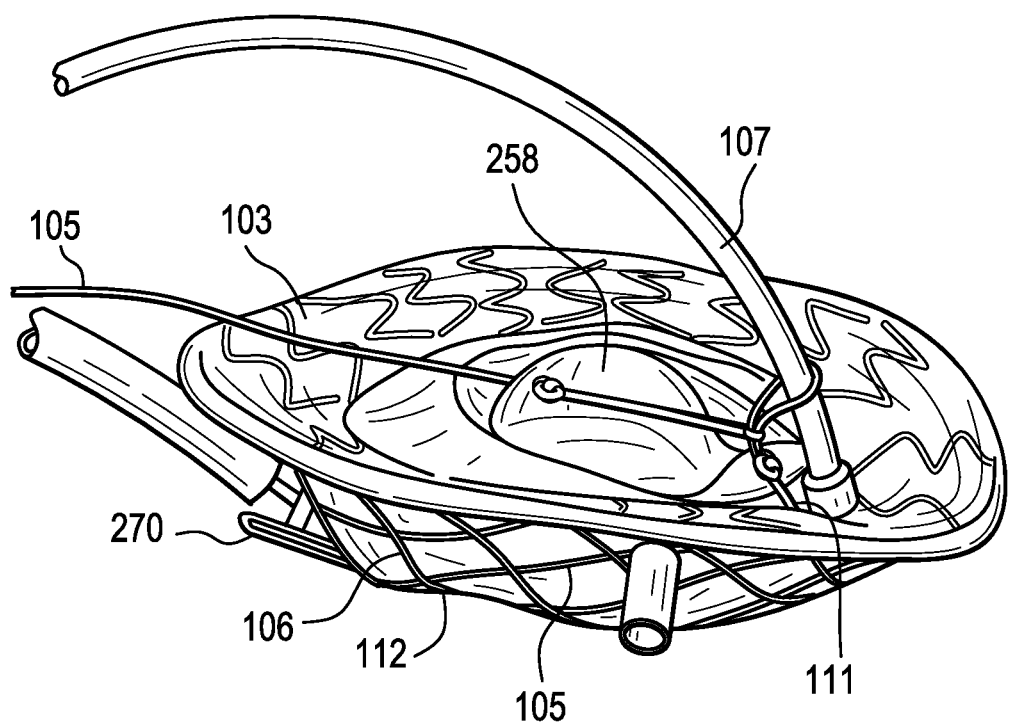
FIG. 5 is an image of one embodiment of the present invention, with cinching assembly attached to the orthogonally deliverable valve.

FIG. 5 is an image of one embodiment of the present invention, with cinching assembly attached to the orthogonally deliverable valve. FIG. 5 shows the valve having valve cuff/collar 103 circumscribing the top edge of cylindrical valve body, with valve leaflet 258 disposed in a flow control component 130 mounted within the axial lumen of the valve body, and a pierceable seal mounted adjacent the flow control component.

FIG. 5 also shows a cinching system 105-107-111 exemplified in a non-limiting aspect with a steerable catheter/control cable 107 extending from a transcatheter delivery catheter and temporarily mounted into a receiver element in a distal portion of the collar 103. The steerable catheter is threaded through a cinching loop on a cinching tether 105, and the cinching tether is strung through an eyelet 111 in the collar 103 between the steerable catheter, and a tether mount 112 on the valve body, with cinching tether loop disposed at an above-collar, atrial side position, and cinching tether mount 112 disposed below the collar.

FIG. 5 shows that by pulling the pulling tether 105, it will apply a radially compressive, or cinching force on the valve body, so that, while the distal side is held against the annular ring, the proximal side can be positioned and lowered into the annular ring, and when released, causes a tension fit of the valve into the annulus.

FIG. 5 also shows a proximal anchoring tab 270 attached to a proximal tab control catheter. The proximal anchoring tab starts in a folded or stowed configuration, and after the valve body has been shoe-horned into the annulus, the proximal anchoring tab can be unfolded or released to extend away from the valve body and provide a subannular anchoring force (upward) on the proximal side. The upward force of the lower proximal anchor is balanced against the proximal side collar providing a supra-annular downward force. Similarly, on the distal side, the distal collar (downward force, ventricular direction), and the distal anchoring tab (upward force, atrial direction), provide upper and lower sandwiching anchoring mechanisms for the valve.

Figure 6:
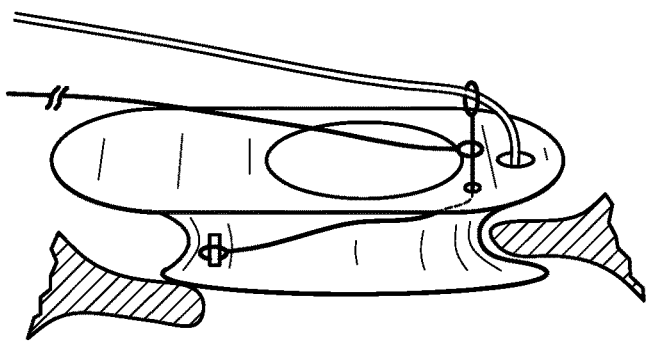
FIG. 6 is an illustration of one embodiment of a valve prior to cinching, with proximal side blocked in a supra-annular (atrial) position, and distal side partially seated onto the annular ring with distal subannular (ventricular) tab and distal atrial cuff forming distal concave circumferential channel in the valve perimeter wall.

FIG. 6 is an illustration of one embodiment of a valve prior to cinching, with proximal side blocked in a supra-annular (atrial) position, and distal side partially seated onto the annular ring with distal subannular (ventricular) tab and distal atrial cuff forming distal concave circumferential channel in the valve perimeter wall.

Figure 7:
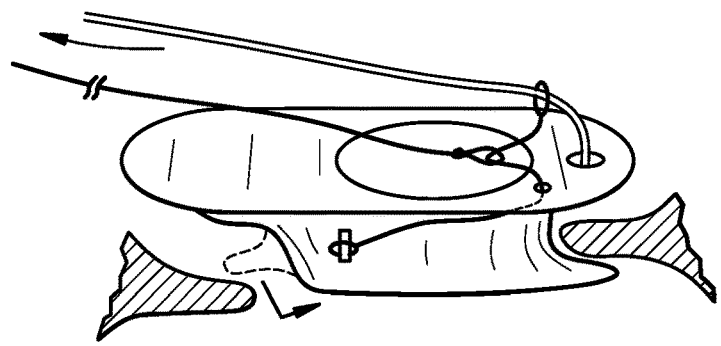
FIG. 7 is an illustration of one embodiment of a valve during cinching, with proximal side cinched or temporarily retracted inwards to allow the proximal side of the valve to be inserted down into the valve annulus, such that by shoe-horning (or adapting) the proximal side into the annulus, the proximal side can be released to move it from a supra-annular position to an annular position, and provide a tension fit against the annular ring. Distal side is shown partially seated onto the annular ring with distal subannular (ventricular) tab and distal atrial cuff forming distal concave circumferential channel in the valve perimeter wall.

FIG. 7 is an illustration of one embodiment of a valve during cinching, with proximal side cinched or temporarily retracted inwards to allow the proximal side of the valve to be inserted down into the valve annulus, such that by shoe-horning (or adapting) the proximal side into the annulus, the proximal side can be released to move it from a supra-annular position to an annular position, and provide a tension fit against the annular ring. Distal side is shown partially seated onto the annular ring with distal subannular (ventricular) tab and distal atrial cuff forming distal concave circumferential channel in the valve perimeter wall.

Figure 8:
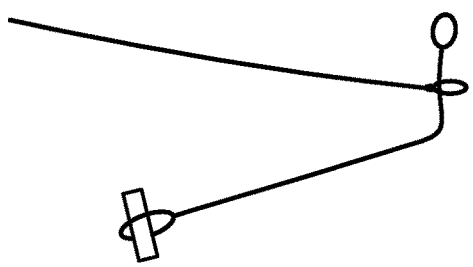
FIG. 8 is an illustration showing one non-limiting embodiment of a cinching system as step 1 of 3 in a released position, whereby the pulling tether and the attached pulling loop has snared the atrial portion (above the valve collar) of the cinching tether, while cinching tether is strung through an eyelet in the collar between a lower mounting element attached to the perimeter wall below the collar and an upper mounting element, that is shown as a cinching loop that is fastened to an anchored steerable catheter where the steerable catheter is threaded through the cinching loop.

FIG. 8 is an illustration showing one non-limiting embodiment of a cinching system as step 1 of 3 in a released position, whereby the pulling tether and the attached pulling loop has snared the atrial portion (above the valve collar) of the cinching tether, while cinching tether is strung through an eyelet in the collar between a lower mounting element attached to the perimeter wall below the collar and an upper mounting element, that is shown as a cinching loop that is fastened to an anchored steerable catheter where the steerable catheter is threaded through the cinching loop.

Figure 9:
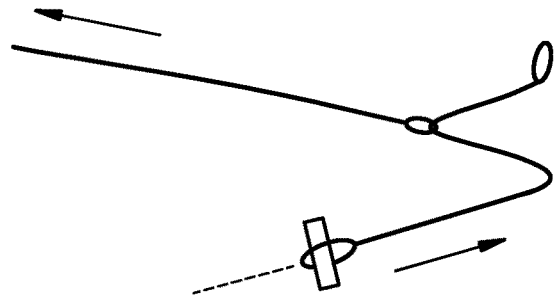
FIG. 9 is an illustration showing one non-limiting embodiment of a cinching system as step 2 of 3 in a cinched position, whereby the pulling tether and the attached pulling loop has snared and pulled the atrial portion (above the valve collar) of the cinching tether, with the lower portion (below collar) of the cinching tether fore-shortened and pulling the valve frame perimeter wall to a (body) compressed position, with cinching tether strung through an eyelet in the collar between a lower mounting element attached to the perimeter wall below the collar and an upper mounting element, that is shown as a cinching loop that is fastened to an anchored steerable catheter where the steerable catheter is threaded through the cinching loop.

FIG. 9 is an illustration showing one non-limiting embodiment of a cinching system as step 2 of 3 in a cinched position, whereby the pulling tether and the attached pulling loop has snared and pulled the atrial portion (above the valve collar) of the cinching tether, with the lower portion (below collar) of the cinching tether fore-shortened and pulling the valve frame perimeter wall to a (body) compressed position, with cinching tether strung through an eyelet in the collar between a lower mounting element attached to the perimeter wall below the collar and an upper mounting element, that is shown as a cinching loop that is fastened to an anchored steerable catheter where the steerable catheter is threaded through the cinching loop.

Figure 10:
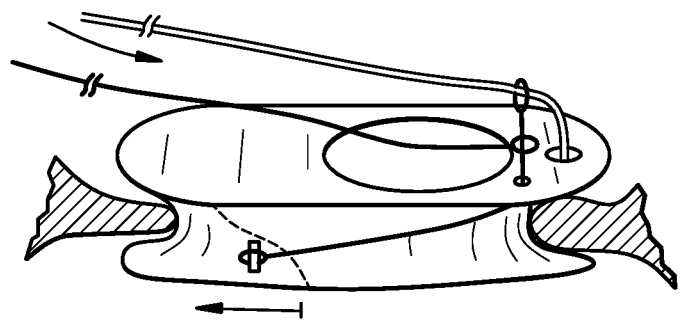
FIG. 10 is an illustration showing one non-limiting embodiment of a cinching system as step 3 of 3 back to a released position, whereby the valve has been seated into the native annulus by lowering the cinched/compressed proximal side perimeter wall into the annular ring and releasing the cinch system to expand the perimeter wall against the proximal side of the native annulus.

FIG. 10 is an illustration showing one non-limiting embodiment of a cinching system as step 3 of 3 back to a released position, whereby the valve has been seated into the native annulus by lowering the cinched/compressed proximal side perimeter wall into the annular ring and releasing the cinch system to expand the perimeter wall against the proximal side of the native annulus.

Figure 11:
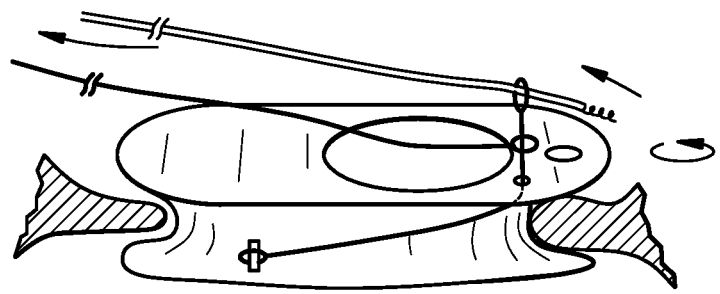
FIG. 11 is an illustration showing one non-limiting embodiment of a cinching system showing the steerable catheter being actuated (rotated, unscrewed) to disengage from the (threaded) receiver.

FIG. 11 is an illustration showing one non-limiting embodiment of a cinching system showing the steerable catheter being actuated (rotated, unscrewed) to disengage from the (threaded) receiver.

Figure 12:
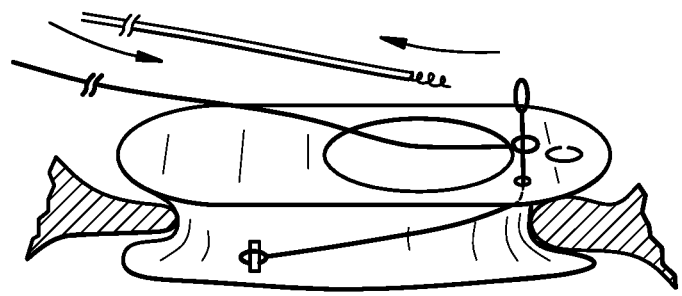
FIG. 12 is an illustration showing one non-limiting embodiment of a cinching system and shows the steerable catheter pulled out of the cinching loop/eyelet of the cinching tether, with the steerable catheter being entirely withdrawn back into a delivery catheter and out of the patient.

FIG. 12 is an illustration showing one non-limiting embodiment of a cinching system and shows the steerable catheter pulled out of the cinching loop/eyelet of the cinching tether, with the steerable catheter being entirely withdrawn back into a delivery catheter and out of the patient.

Figure 13:
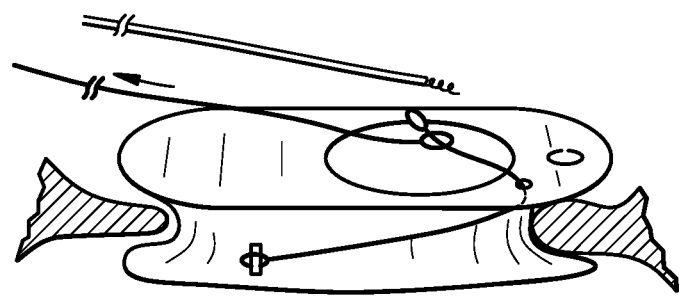
FIG. 13 is an illustration showing one non-limiting embodiment of a cinching system and shows the pulling tether and its loop pulled out of the cinching loop/eyelet of the cinching tether, with the pulling tether being entirely withdrawn back into a delivery catheter and out of the patient.

FIG. 13 is an illustration showing one non-limiting embodiment of a cinching system and shows the pulling tether and its loop pulled out of the cinching loop/eyelet of the cinching tether, with the pulling tether being entirely withdrawn back into a delivery catheter and out of the patient.

Figure 14:
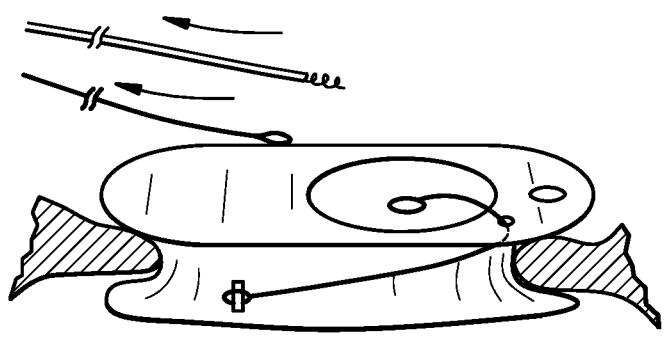
FIG. 14 is another illustration showing one non-limiting embodiment of a cinching system and shows the steerable catheter and the pulling tether and its loop pulled out of the cinching loop/eyelet of the cinching tether, with the steerable catheter and the pulling tether being entirely withdrawn back into a delivery catheter and out of the patient.

FIG. 14 is another illustration showing one non-limiting embodiment of a cinching system and shows the steerable catheter and the pulling tether and its loop pulled out of the cinching loop/eyelet of the cinching tether, with the steerable catheter and the pulling tether being entirely withdrawn back into a delivery catheter and out of the patient.

Figure 15:
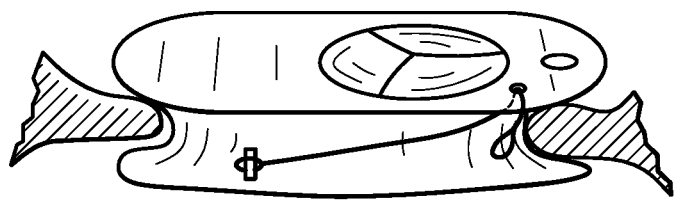
FIG. 15 is an illustration of the deployed/seated valve with cinching tether either available to be trimmed off, or left in place to be subsumed into the in-growth tissue.

FIG. 15 is an illustration of the deployed/seated valve with cinching tether either available to be trimmed off, or left in place to be subsumed into the in-growth tissue.

Figure 16:
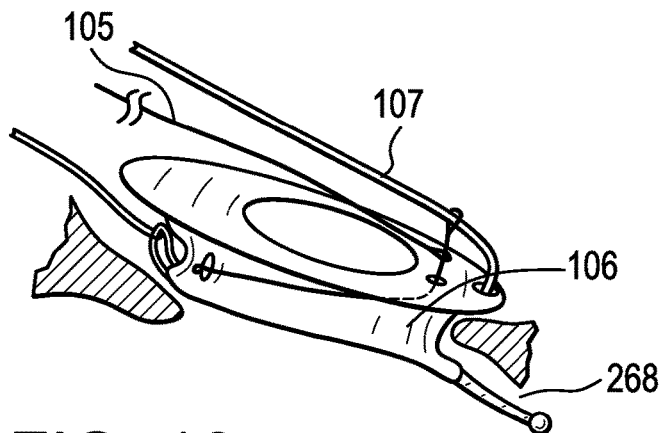
FIG. 16 is an illustration showing one non-limiting embodiment of step 1 of 4 of a delivery process for an orthogonally delivered prosthetic heart valve having a distal anchoring tab/tension arm placed into a distal subannular position with distal perimeter wall wedged onto the native annular ring, a folded/stowed proximal tab attached to a proximal tab catheter, and a cinching system installed onto the valve.

FIG. 16 is an illustration showing one non-limiting embodiment of step 1 of 4 of a delivery process for an orthogonally delivered prosthetic heart valve having a distal anchoring tab/tension arm 258 placed into a distal subannular position with distal perimeter wall wedged onto the native annular ring, a folded/stowed proximal tab 270 attached to a proximal tab catheter, and a cinching system 105-107-111-112 installed onto the valve.

Figure 17:
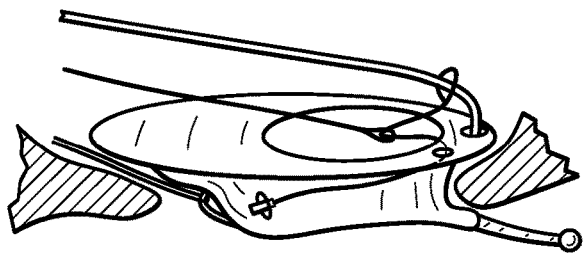
FIG. 17 is an illustration showing one non-limiting embodiment of step 2 of 4 of a delivery process for an orthogonally delivered prosthetic heart valve and shows the proximal side of the valve body (perimeter wall) cinched/retracted inwards to reduce the size (diameter, circumference) of the valve body so the valve can be seated into the native annulus.

FIG. 17 is an illustration showing one non-limiting embodiment of step 2 of 4 of a delivery process for an orthogonally delivered prosthetic heart valve and shows the proximal side of the valve body (perimeter wall) cinched/retracted inwards to reduce the size (diameter, circumference) of the valve body so the valve can be seated into the native annulus.

Figure 18:
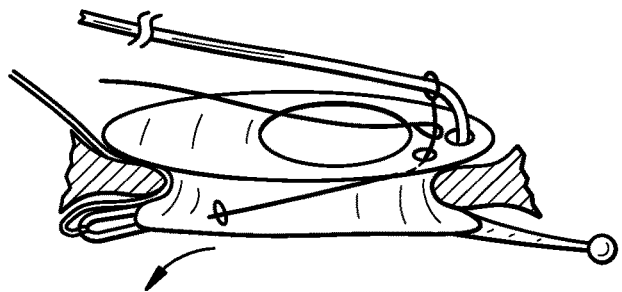
FIG. 18 is an illustration showing one non-limiting embodiment of step 3 of 4 of a delivery process for an orthogonally delivered prosthetic heart valve and shows both the release of the cinch, and the deployment of the proximal tab, with cinching system releasing the compressive force on the valve body and allowing the valve to expand radially into the native annulus, and with the proximal tab catheter unfolding the folded/stowed proximal tab away from the valve body to provide a proximal side anchoring element for the valve.

FIG. 18 is an illustration showing one non-limiting embodiment of step 3 of 4 of a delivery process for an orthogonally delivered prosthetic heart valve and shows both the release of the cinch, and the deployment of the proximal tab, with cinching system releasing the compressive force on the valve body and allowing the valve to expand radially into the native annulus, and with the proximal tab catheter unfolding the folded/stowed proximal tab away from the valve body to provide a proximal side anchoring element for the valve.

Figure 19:
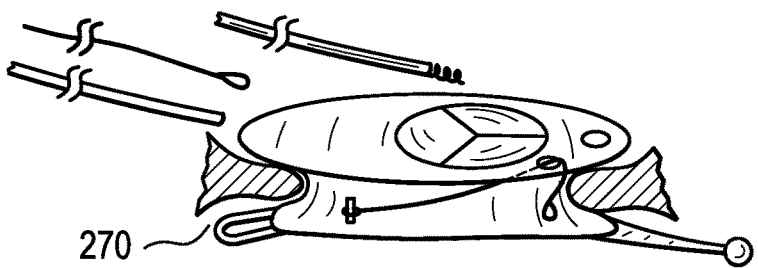
FIG. 19 is an illustration showing one non-limiting embodiment of step 4 of 4 of a delivery process for an orthogonally delivered prosthetic heart valve where the valve has been deployed and the cinching system and the proximal tab catheter are being withdrawn into the delivery catheter and out of the patient.

FIG. 19 is an illustration showing one non-limiting embodiment of step 4 of 4 of a delivery process for an orthogonally delivered prosthetic heart valve where the valve has been deployed and the cinching system and the proximal tab catheter are being withdrawn into the delivery catheter and out of the patient.

Figure 20:
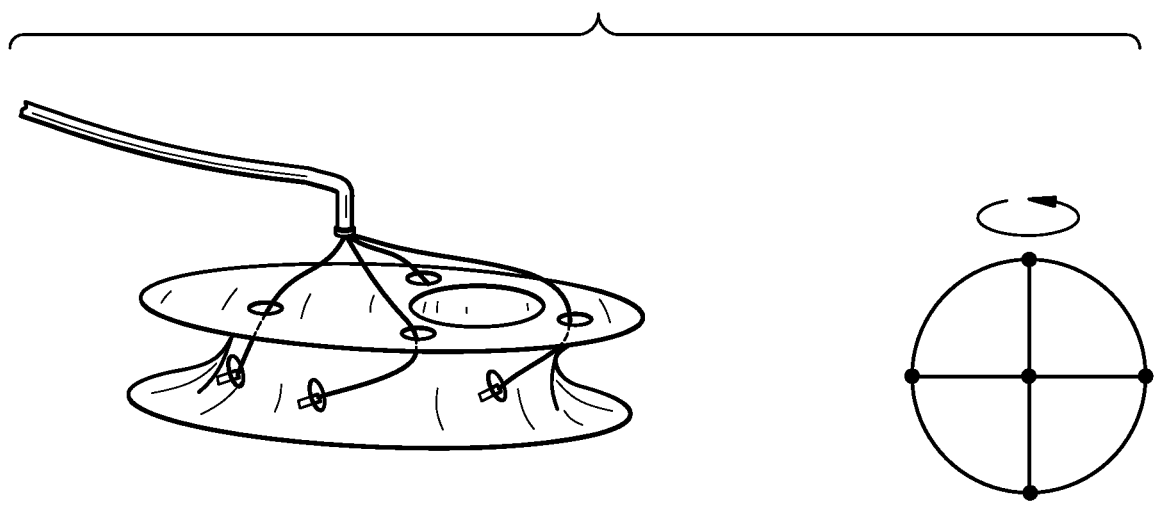
FIG. 20 is an illustration showing step 1 of 2 of one non-limiting preferred twisting embodiment of a cinching system, with the valve in an expanded configuration, and a steerable catheter connected to multiple pulling and cinching (combination) tethers, with each tether strung through separate eyelets in the collar and mounted below the collar of the valve onto the valve body wall, where rotation of the steerable catheter fore-shortens the tethers and twists or wrings the valve body to a narrower radial size to facilitate insertion and positioning into the native annulus.

FIG. 20 is an illustration showing step 1 of 2 of one non-limiting preferred twisting embodiment of a cinching system, with the valve in an expanded configuration, and a steerable catheter connected to multiple pulling and cinching (combination) tethers, with each tether strung through separate eyelets in the collar and mounted below the collar of the valve onto the valve body wall, where rotation of the steerable catheter fore-shortens the tethers and twists or wrings the valve body to a narrower radial size to facilitate insertion and positioning into the native annulus.

Figure 21:
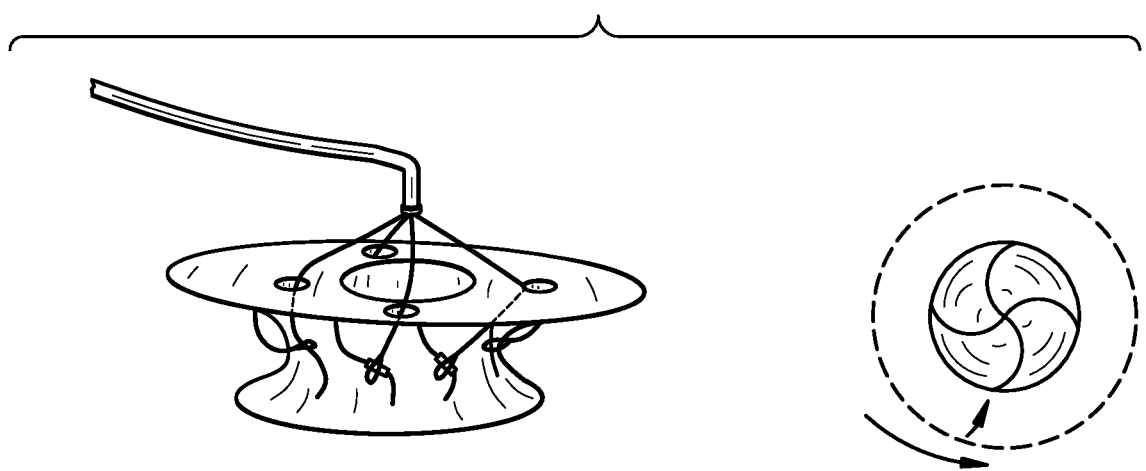
FIG. 21 is an illustration showing step 2 of 2 of one non-limiting preferred twisting embodiment of a cinching system, with the valve in a radially compressed configuration, where rotation of the steerable catheter has fore-shortened the tethers thereby twisting or wringing the valve body to a narrower radial size to facilitate insertion and positioning of the valve into the native annulus.

FIG. 21 is an illustration showing step 2 of 2 of one non-limiting preferred twisting embodiment of a cinching system, with the valve in a radially compressed configuration, where rotation of the steerable catheter has fore-shortened the tethers thereby twisting or wringing the valve body to a narrower radial size to facilitate insertion and positioning of the valve into the native annulus.

Figure 22:
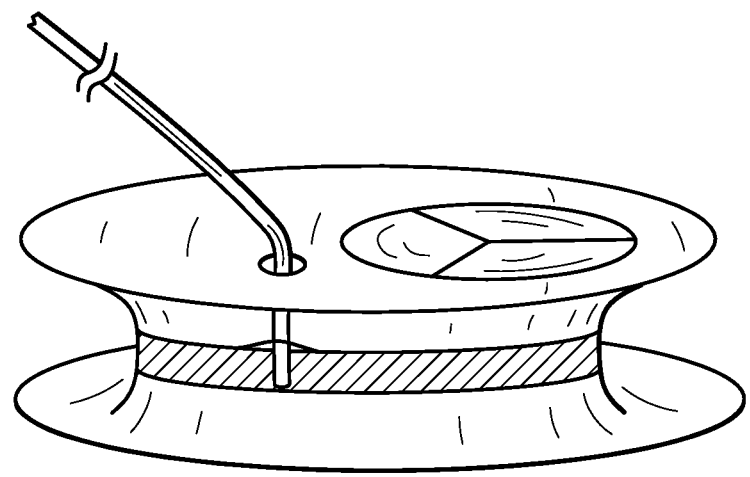
FIG. 22 is an illustration showing step 1 of 2 of one non-limiting preferred belted embodiment of a cinching system, with the valve in an expanded configuration, and a steerable catheter connected to roller cylinder, with a cinchable belt encircling the valve body and mounted below the collar of the valve onto the valve body wall, where rotation of the steerable catheter rotates the roller cylinder and fore-shortens the cinchable belt to reduce the valve body to a narrower radial size to facilitate insertion and positioning into the native annulus.

FIG. 22 is an illustration showing step 1 of 2 of one non-limiting preferred belted embodiment of a cinching system, with the valve in an expanded configuration, and a steerable catheter connected to roller cylinder, with a cinchable belt encircling the valve body and mounted below the collar of the valve onto the valve body wall, where rotation of the steerable catheter rotates the roller cylinder and fore-shortens the cinchable belt to reduce the valve body to a narrower radial size to facilitate insertion and positioning into the native annulus.

Figure 23:
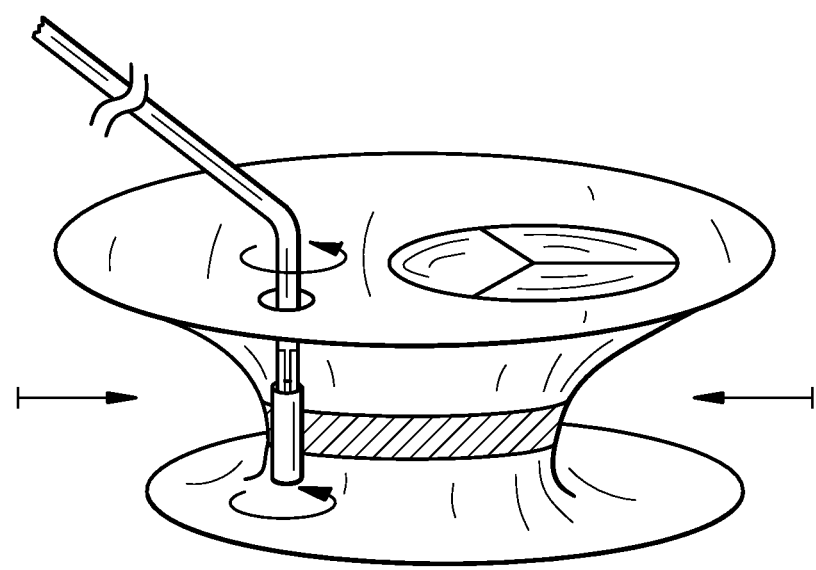
FIG. 23 is an illustration showing step 2 of 2 of one non-limiting preferred cinchable belt embodiment of a cinching system, with the valve in a radially compressed configuration, where rotation of the steerable catheter has rolled a portion of the belt onto the roller cylinder, and has fore-shortened the belt reducing the valve body to a narrower radial size to facilitate insertion and positioning of the valve into the native annulus.

FIG. 23 is an illustration showing step 2 of 2 of one non-limiting preferred cinchable belt embodiment of a cinching system, with the valve in a radially compressed configuration, where rotation of the steerable catheter has rolled a portion of the belt onto the roller cylinder, and has fore-shortened the belt reducing the valve body to a narrower radial size to facilitate insertion and positioning of the valve into the native annulus.

Figure 24:
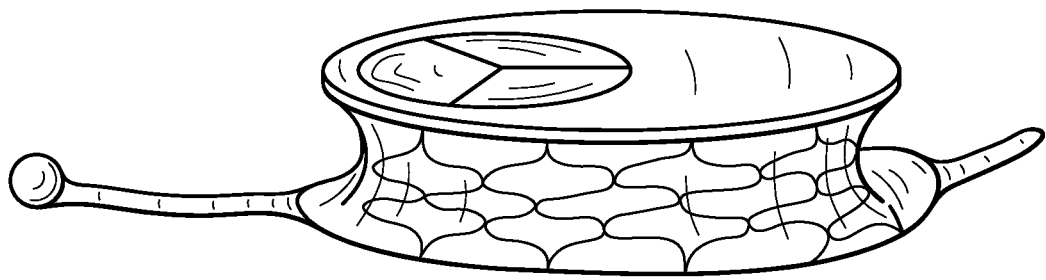
FIG. 24 is an illustration of a side perspective view of an orthogonally deliverable transcatheter heart valve with distal right ventricular outflow tract (RVOT) tab, a proximal tab according to the invention.

FIG. 24 is an illustration of a side perspective view of an orthogonally deliverable transcatheter heart valve with distal right ventricular outflow tract (RVOT) tab, a proximal tab according to the invention.

Figure 25:
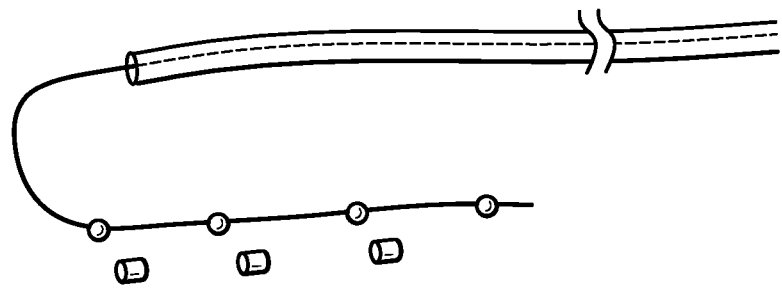
FIG. 25 is an illustration of a side view of a single tether cinch according to the invention having a delivery catheter sheathed over releasable tether lock encircling the perimeter wall and anchor mountable elements for connecting to the tether lock.

FIG. 25 is an illustration of a side view of a single tether cinch according to the invention having a delivery catheter sheathed over releasable tether lock encircling the perimeter wall and anchor mountable elements for connecting to the tether lock.

Figure 26:
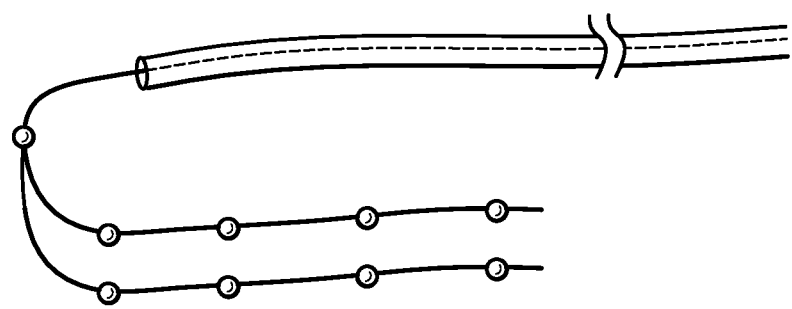
FIG. 26 is an illustration of a side view of a double tether cinch according to the invention having a delivery catheter sheathed over releasable tether lock encircling the perimeter wall and anchor mountable elements for connecting to the tether lock.

FIG. 26 is an illustration of a side view of a double tether cinch according to the invention having a delivery catheter sheathed over releasable tether lock encircling the perimeter wall and anchor mountable elements for connecting to the tether lock.

Figure 27:
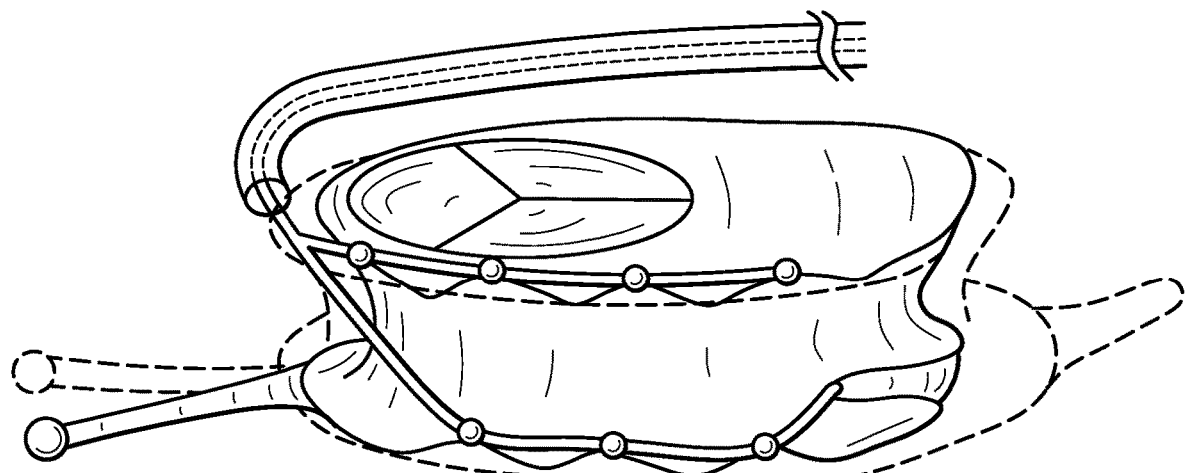
FIG. 27 is an illustration of a side view of a double tether cinch according to the invention having a delivery catheter sheathed over releasable tether lock encircling the perimeter wall and anchor mountable elements for connecting to the tether lock, and to the folded up proximal tab.

FIG. 27 is an illustration of a side view of a double tether cinch according to the invention having a delivery catheter sheathed over releasable tether lock encircling the perimeter wall and anchor mountable elements for connecting to the tether lock, and to the folded up proximal tab.

Figure 28:
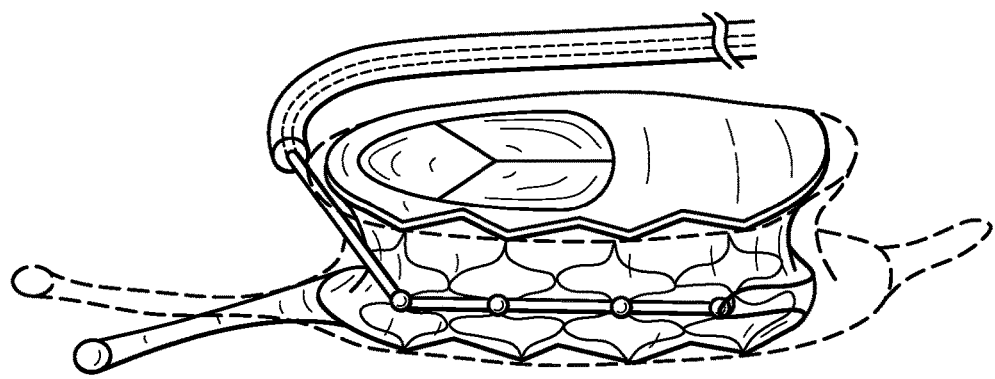
FIG. 28 is an illustration of a side view of a single tether cinch according to the invention having a delivery catheter sheathed over releasable tether lock encircling the perimeter wall and anchor mountable elements for connecting to the tether lock, and to the folded up proximal tab.

FIG. 28 is a side view illustration of valve in a cinched configuration.

Figure 29:
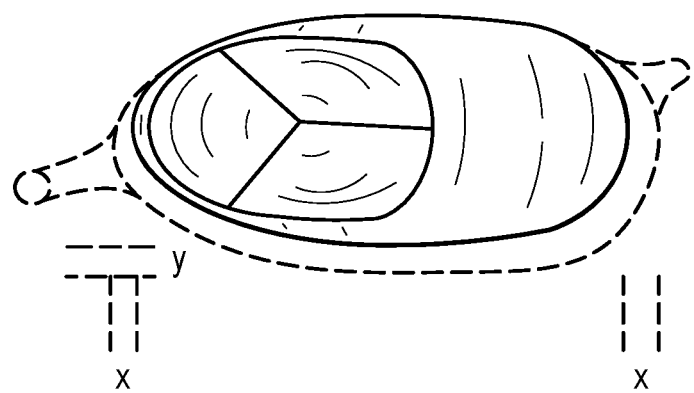
FIG. 29 is a top view illustration of a valve in a cinched configuration.

FIG. 29 is a top view illustration of a valve in a cinched configuration.

Figure 30:
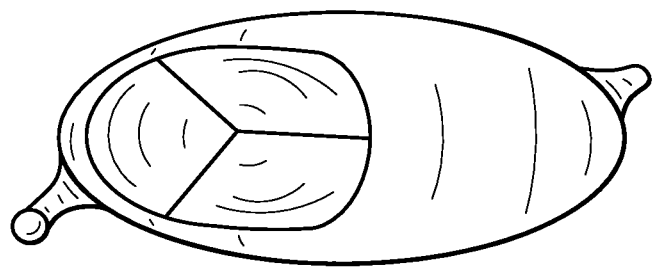
FIG. 30 is a top view illustration of a valve in an expanded configuration.

FIG. 30 is a top view illustration of a valve in an expanded configuration.

Figure 31:
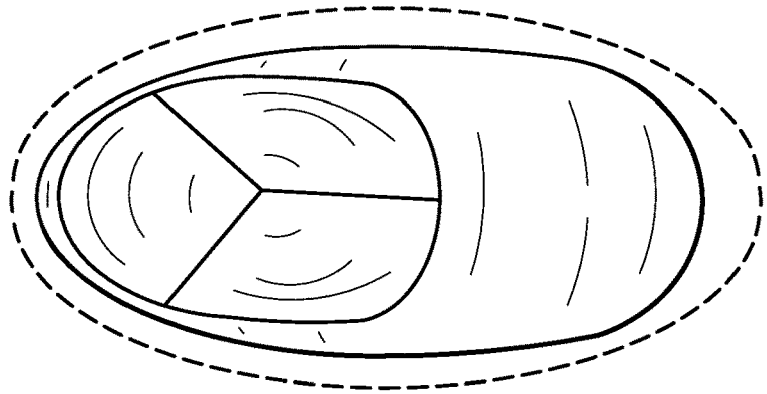
FIG. 31 is a top view illustration of a valve in a double sided cinched configuration (septal and anterior, both cinched).

FIG. 31 is a top view illustration of a valve in a double sided cinched configuration (septal and anterior, both cinched).

Figure 32:
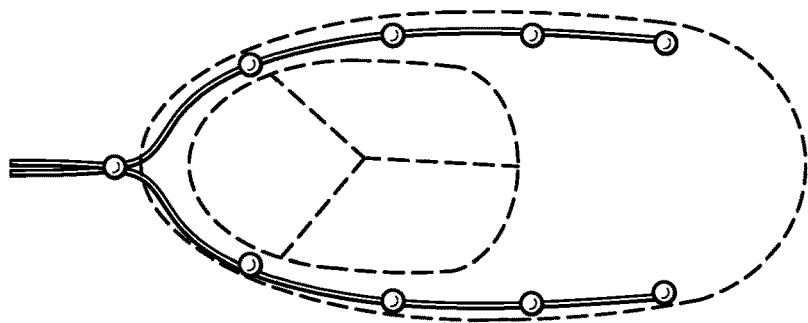
FIG. 32 is a top view illustration of a valve having the tether installed, in a double sided expanded configuration (septal and anterior, both expanded).

FIG. 32 is a top view illustration of a valve having the tether installed, in a double sided expanded configuration (septal and anterior, both expanded).

Figure 33:
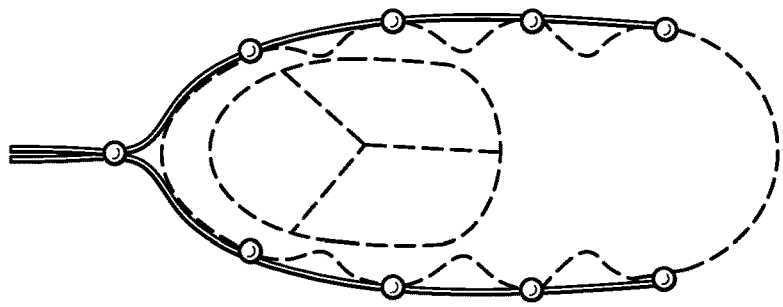
FIG. 33 is a top view illustration of a valve having the tether installed, in a double sided cinched configuration (septal and anterior, both cinched).

FIG. 33 is a top view illustration of a valve having the tether installed, in a double sided cinched configuration (septal and anterior, both cinched).

FIG. 34 is a chart showing the percentage reduction of the long-axis R1 of the ellipse of the valve and the calculated shrinkage of the circumference.

FIG. 35 is a chart showing the percentage reduction of the short-axis r1 of the ellipse of the valve and the calculated shrinkage of the circumference.

FIG. 36 is a chart showing the percentage reduction of the long-axis R1 of the ellipse of the valve and the calculated shrinkage of the circumference.

Figure 37:
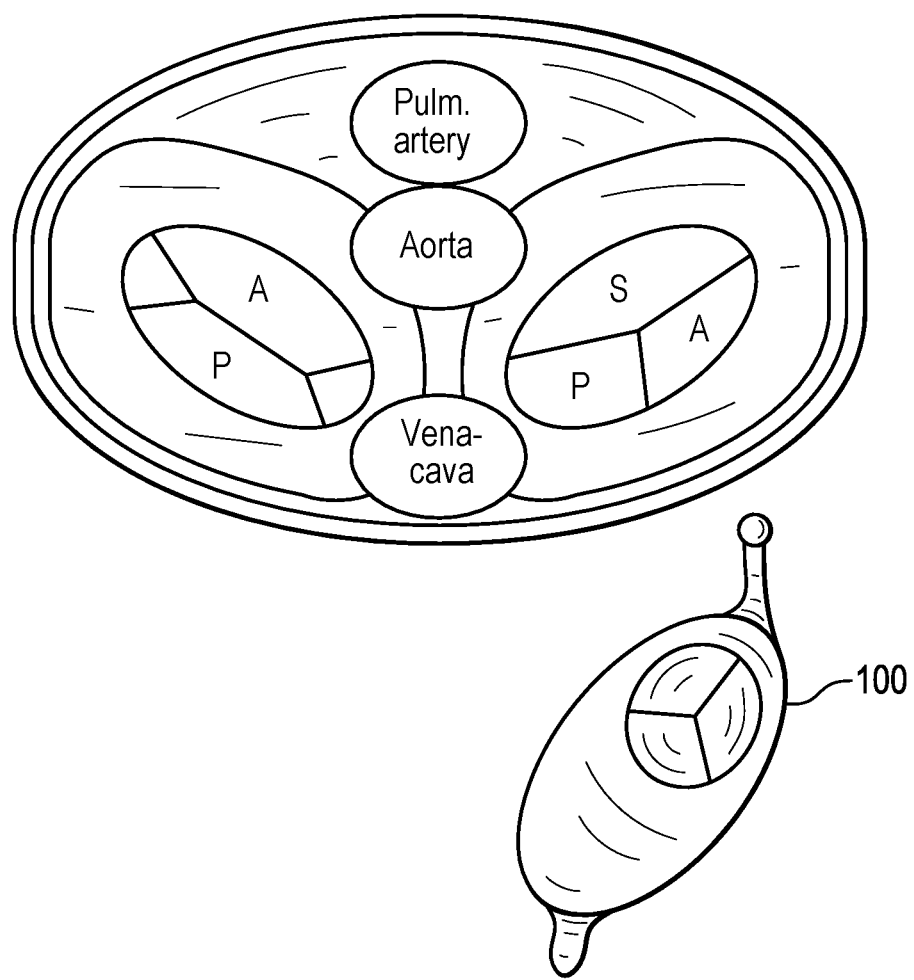
FIG. 37 is a top (nadir) view of the heart in cross section and show the relationship between the various anatomical features.

FIG. 37 is a top (nadir) view of the heart in cross section and show the relationship between the various anatomical features.

FIGS. 38A to 38D illustrate a process of (FIG. 38A) a valve delivery catheter working in conjunction with a cinching apparatus catheter to deliver the valve to the native annulus, (FIG. 38B) position a distal subannular anchoring tab, and then (FIG. 38C) seat and release/uncinch the valve to effectuate a good seal simultaneous with more predictable seating of the valve in the annulus, and then (FIG. 38D) extend the proximal subannular anchoring tab.

FIG. 39 is an illustration of one type of wire frame panel showing a wire frame configuration that is balanced between horizontal compression and lateral compression.

FIG. 40 is an illustration of one type of wire frame panel showing a wire frame configuration that is weighted more towards horizontal compression than lateral compression.

FIG. 41 is an illustration of a percutaneously delivered prosthetic tricuspid valve via the femoral vein.

FIG. 42 is an illustration of one type of wire frame panel showing a wire frame configuration that is weighted more towards horizontal compression than lateral compression.

FIG. 43 is an illustration of one type of wire frame panel showing a wire frame configuration that is balanced between horizontal compression and lateral compression.

Figure 44:
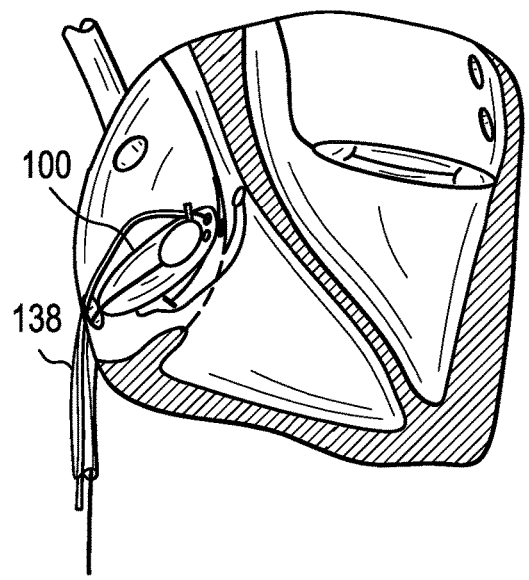
FIG. 44 is an illustration of a valve cinched and being seated in the tricuspid valve annulus.

FIG. 44 is an illustration of a valve 100 cinched and being seated in the tricuspid valve annulus, with delivery catheter 138 accessing through the IVC.

Figure 45:
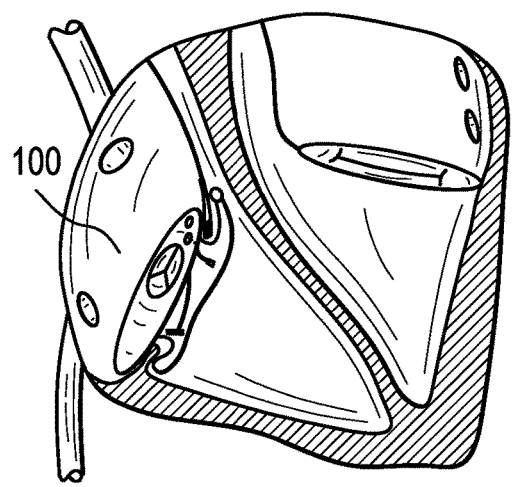
FIG. 45 is an illustration of a valve released after being cinched and seated in the tricuspid valve annulus
Figure 46:
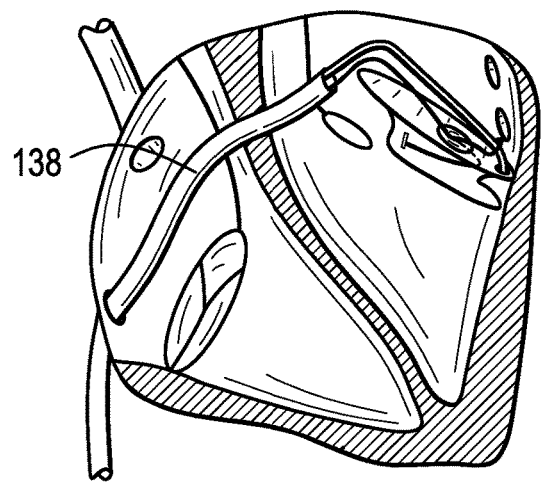
FIG. 46 is an illustration of a valve cinched and being seated in the mitral valve annulus.

FIG. 45 is an illustration of a valve 100 released after being cinched and seated in the tricuspid valve annulus FIG. 46 is an illustration of a valve 100 cinched and being seated in the mitral valve annulus.

Figure 47:
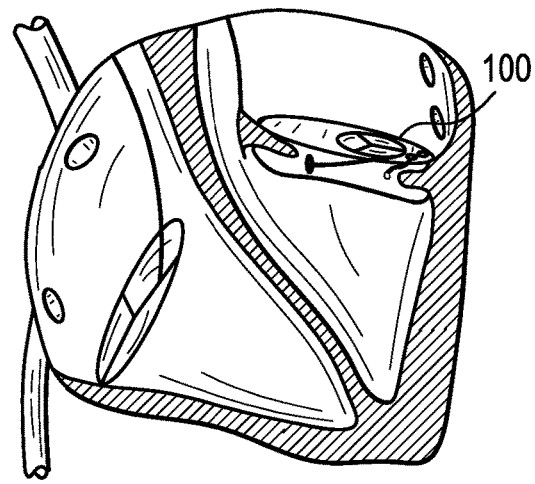
FIG. 47 is an illustration of a valve released after being cinched and seated in the mitral valve annulus.

FIG. 47 is an illustration of a valve 100 released after being cinched and seated in the mitral valve annulus, with delivery catheter 138 accessing through the IVC via a trans-septal puncture.

Figure 48:
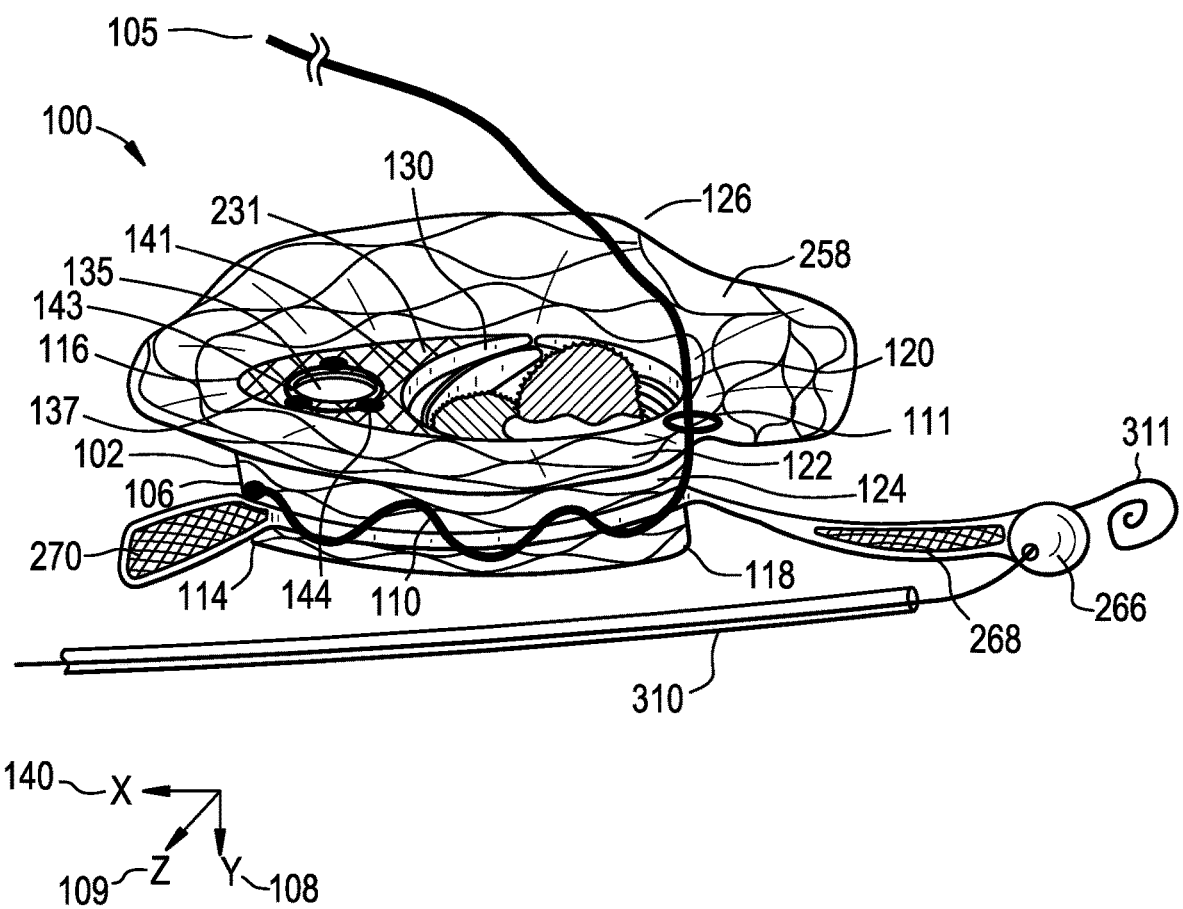
FIG. 48 is an illustration of a side perspective view of an inner regurgitation control component with radio-opaque markers as part of an orthogonally deliverable transcatheter heart valve with a collapsible flow control component mounted within the annular outer support frame, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, and the valve having a superelastic wire loop distal tab and a superelastic wire loop proximal tab according to the invention.

Referring again to the drawings, FIG. 48 is an illustration of a side perspective view of an orthogonally deliverable transcatheter heart valve 100 with annular outer support frame 102, a collapsible flow control component 130 mounted within the annular outer support frame 102, distal tab 268 and proximal tab 270, according to the invention. FIG. 48 shows tether 105, control cable 107, and tether eyelet 111. Proximal wall 114 is shown here in an expanded configuration.

The inner regurgitation control component 135 is comprised of tissue cover 141, reinforcement ring 143, radiopaque markers 144, and drum/regurgitation channel 135.

The collapsible (inner) flow control component 130 has leaflet frame 231 with 2-4 flexible leaflets 258 mounted thereon, the leaflet frame 231 foldable along a z-axis 109 from a cylindrical configuration to a flattened cylinder configuration and compressible along a vertical axis 108 (y-axis) to a shortened configuration.

The annular outer support frame 102 is made from a shape-memory material such as nickel-titanium alloy, for example nitinol, and is therefore a self-expanding structure starting from a compressed configuration. The annular (outer) support frame 102 has a central (interior) channel and an outer perimeter wall 106 (transannular section) circumscribing a central vertical axis 108, when in an expanded configuration, and said annular outer support frame 102 having a distal side 118 and a proximal side 114.

The flow control component 130 is mounted within the annular outer support frame 102 and is configured to permit blood flow in a first direction, e.g., atrial to ventricular, through an inflow end 132 of the valve 100 and block blood flow in a second direction, opposite the first direction, through an outflow end 134 of the valve 100.

The inner regurgitation control component 135, like the inner flow control component 130 and the outer annular frame 102, is foldable and compressible. The inner flow control component 130 comprises leaflet frame 231 with 2-4 flexible leaflets 258 mounted on the leaflet frame 231.

The flow control component 130, and thereby the leaflet frame 231, like the outer frame 102, is foldable along a z-axis (front to back) from a cylindrical configuration to a flattened cylinder configuration, where the fold lines are located on a distal side and on a proximal side, taking the leaflet frame 231 from a ring or cylinder shape, and flattening it from a ring to a two-layer band i.e., folded over on itself, or like a cylinder flattened into a rectangle or square joined along two opposing sides. This allows the outer frame 102 and the flow control component 130 to reduce the radius along z-axis until the side walls are in contact or nearly so.

This also allows the outer frame 102 and the flow control component 130 to maintain the radius along the horizontal axis, the y-axis, to minimize the number of wire cells, which make up the outer and the inner, that are damaged by forces applied during folding and/or compression necessary for loading into the delivery catheter.

The inner regurgitation control component 135, flow control component 130, leaflet frame 231, and the outer frame 102 are also vertically (y-axis) compressible, reducing the height of the entire valve structure to fit within the inner diameter of a delivery catheter 138 (not shown in this figure). By folding in the z-axis and vertically compressing in the y-axis, the valve structure is permitted to maintain a very large dimension along the horizontal, or x-axis. For example, a 60 mm or larger diameter valve can be delivered via transcatheter techniques. The length of the long axis of a valve, e.g., 60 mm, since it runs parallel to the central axis of the delivery catheter, is not limited by the large amount of wire frame and cover material necessary for such a large valve. This is not possible with existing center-axis delivery (axial) transcatheter valves. The use of a folded, compressed valve that is orthogonal to the traditional axial-delivery valves permits treatment options not available previously. FIG. 48 also shows a distal anchoring tab 268 mounted on the distal side 118 of the annular outer support frame 102, and a proximal anchoring tab 270 mounted on the proximal side 114 of the annular outer support frame 102.

In a preferred embodiment, the horizontal x-axis of the valve is at an intersecting angle of between 45-135 degrees to the central vertical y-axis when in an expanded configuration.

In a preferred embodiment, the horizontal x-axis of the compressed configuration of the valve is substantially parallel to a length-wise cylindrical axis of the delivery catheter.

In another preferred embodiment, the valve has a height of about 5-60 mm and a diameter of about 25-80 mm. FIG. 48 also shows guide wire sheath 310, and guide wire 311. Lumen or guide ball 266 is shown mounted on the distal end of the distal tab 268 and having guide wire 311 threaded through the lumen 266. Lumen 266, although large enough in internal diameter to permit the guide wire 311 to extend through, lumen 266 is not large enough in internal diameter to permit the sheath 310 to extend through. This allows sheath 310 to be advanced along the guide wire 311 until it runs up against the proximal side of the lumen 266, wherein continued application of a pushing force on the sheath 310 pushes against the lumen, and allows the valve to be pulled by the distal tab out of the delivery catheter, and to the target location for deploying the valve.

Figure 49:
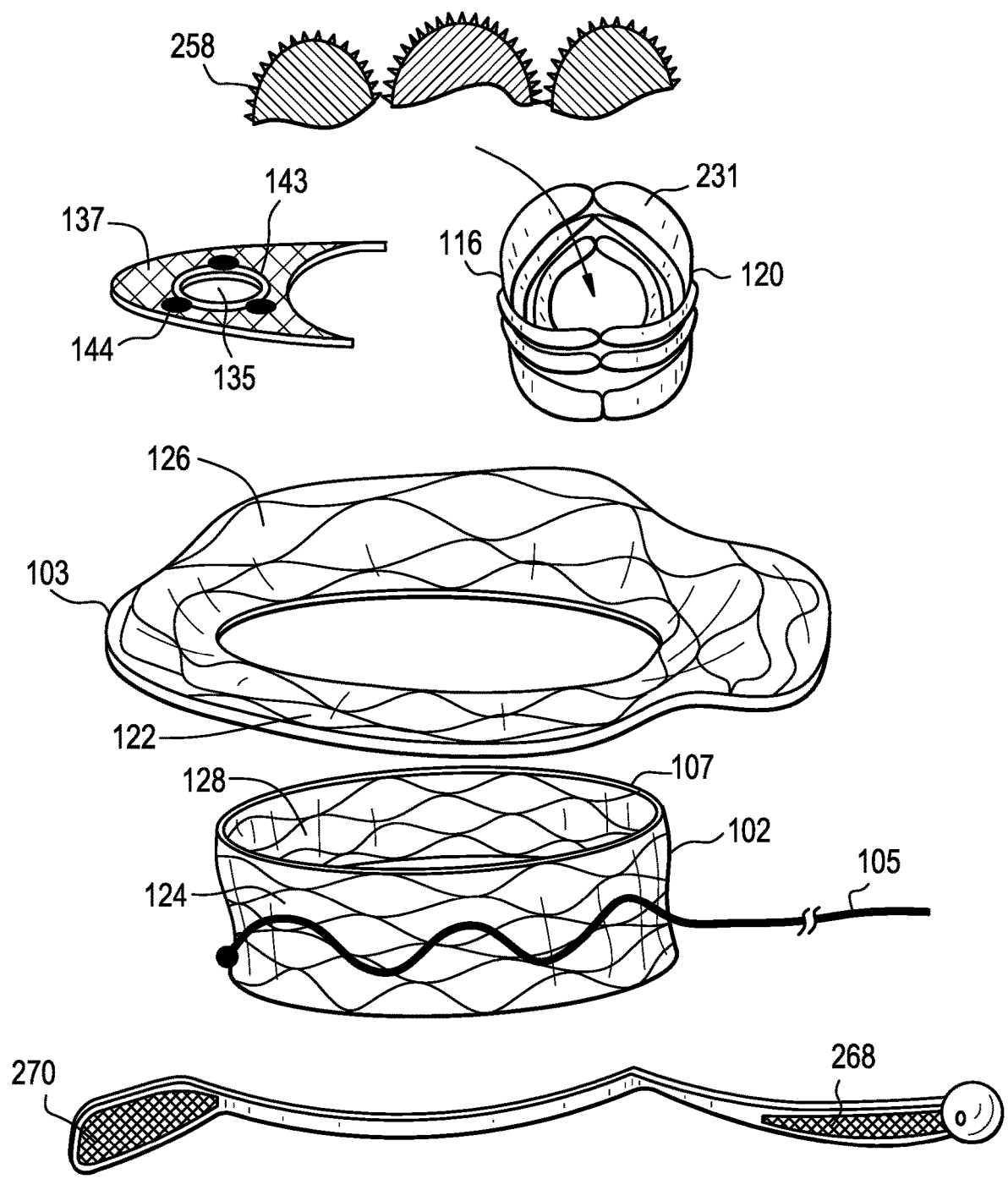
FIG. 49 is an illustration of a side perspective exploded view of an embodiment having an inner regurgitation control component with radio-opaque markers, three leaflet cusp or pockets mounted within a foldable and compressible inner wire frame, the inner is mounted within an outer wire frame which has a collar component attached circumferentially at a top edge of the outer wire frame, a dual tab component, and a mesh component, according to the invention.

FIG. 49 is an illustration of a side perspective view of an exploded view of an embodiment having inner regurgitation drum 137 with markers 144, channel 135, and ring 143. FIG. 49 also shows three leaflet 258 cusps or pockets mounted within a foldable and compressible inner wire frame 231, with distal fold area 120 and proximal fold area 116, the inner 231 is mounted within an outer wire frame 102 which has a collar component 103 attached circumferentially at a top edge 107 of the outer wire frame 102, a dual tab component having a distal (RVOT) tab 268 and a proximal tab 270, and an optional mesh component of biocompatible material that may be used to cover the spacer element 137, to cover the collar 103, to cover the inner and outer aspect of the outer frame 102, and/or to cover the anchoring tabs 268, and 270, according to the invention.

Atrial collar 103 is shaped to conform to the native deployment location. In a tricuspid replacement, the atrial collar will have a tall back wall portion to conform to the septal area of the native valve, and will have a distal and proximal upper collar portion. The distal collar portion can be larger than the proximal upper collar portion to account for the larger flat space above (atrial) the right ventricular outflow tract (RVOT) subannular area.

Figure 50:
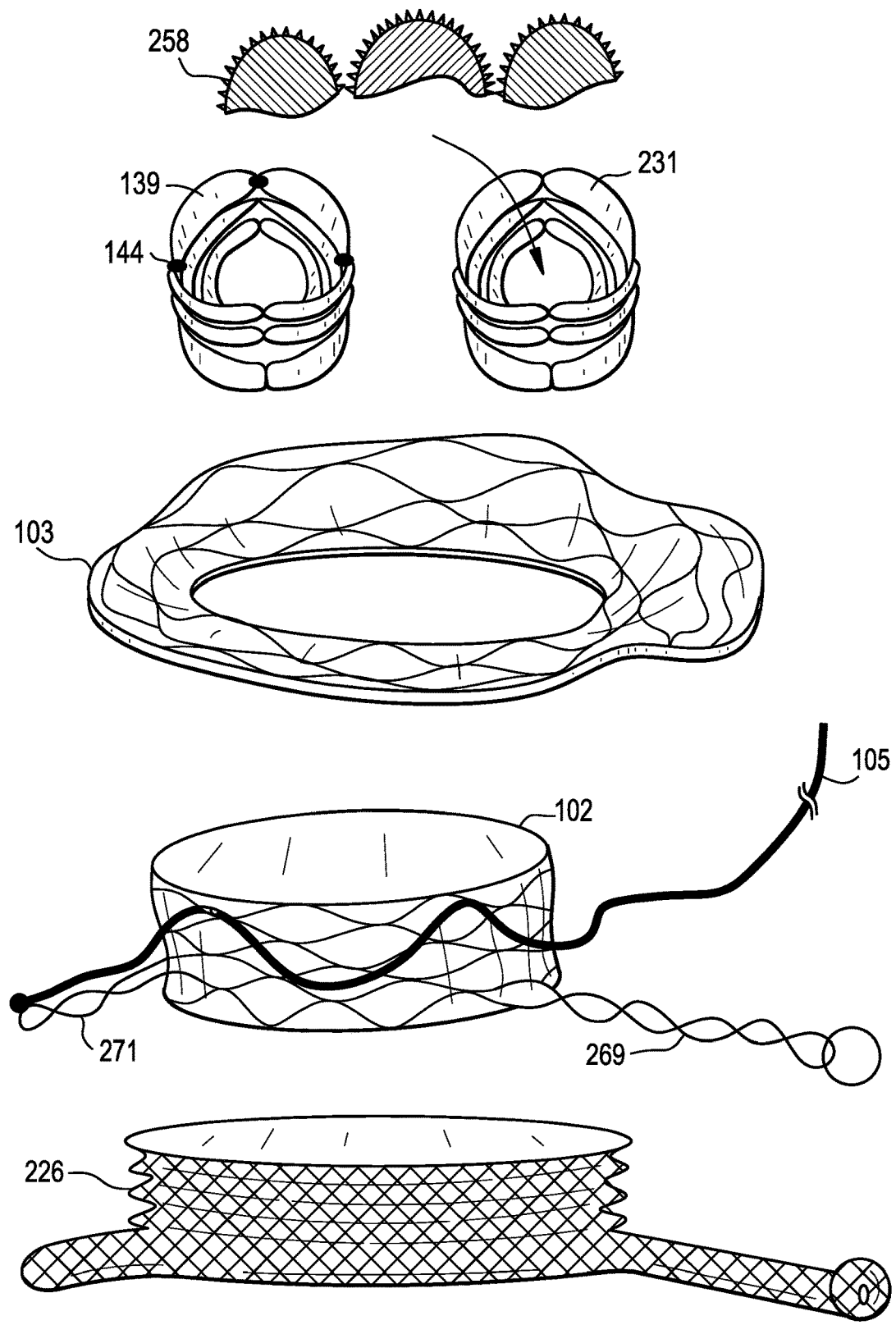
FIG. 50 is an illustration of a side perspective exploded view of an embodiment having an inner regurgitation control component with radio-opaque markers, three leaflet cusp or pockets mounted within a foldable and compressible inner wire frame, the inner is mounted within an outer wire frame which has a collar component attached circumferentially at a top edge of the outer wire frame, a pair of integrated, independent tab components, and a mesh component, according to the invention.

FIG. 50 is an illustration of a side perspective view of an exploded view of an embodiment having an open regurgitation frame 139 having radiopaque markers 144. FIG. 50 also shows three leaflet cusp or pockets 258 mounted within a foldable and compressible inner wire frame 231, the inner 231 is mounted within an outer wire frame 102 which has a collar component 103 attached circumferentially at a top edge 107 of the outer wire frame 102, an uncovered spacer 139, a pair of integrated, independent tab components 269, 270, and a mesh component 226, according to the invention.

Uncovered regurgitation frame 139 provides for controlled regurgitation of the valve. The uncovered regurgitation frame 139 can be later plugged with a later inserted stent or cover or plug once regurgitation is no longer needed by the patient.

Atrial collar 103 is shaped to conform to the native deployment location. In a tricuspid replacement, the atrial collar will have a tall back wall portion to conform to the septal area of the native valve, and will have a distal and proximal upper collar portion. The distal collar portion can be larger than the proximal upper collar portion to account for the larger flat space above (atrial) the right ventricular outflow tract (RVOT) subannular area.

Integrated tabs 269 and 271 are unitary construction with the body of the outer frame. The tabs may vary in size and shape. In a preferred embodiment, the RVOT tab, e.g., 269 may be longer to reach into the entry of the pulmonary artery (in the case of a tricuspid replacement).

Figure 51:
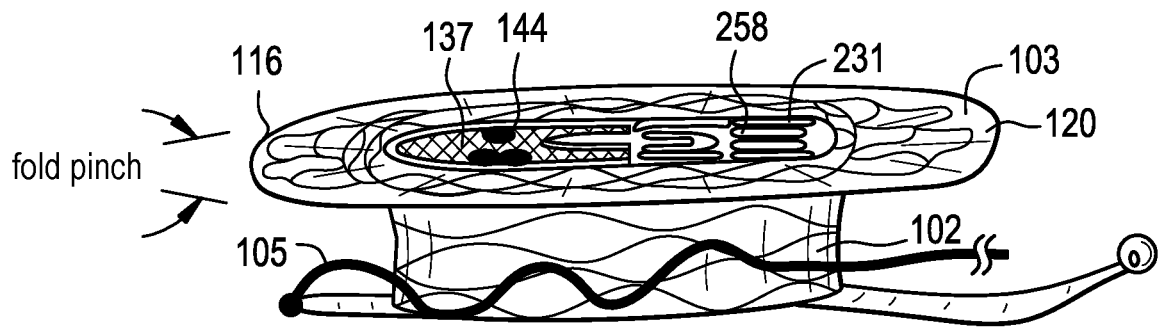
FIG. 51 is an illustration of a side perspective view of an orthogonally deliverable transcatheter heart valve in a folded configuration along the z-axis (front to back when viewed from the broader side) according to the invention.

FIG. 51 is an illustration of a side perspective view of an orthogonally deliverable transcatheter heart valve 100 in a folded configuration along the z-axis (front to back when viewed from the broader side) according to the invention. FIG. 51 shows folded (flattened) outer frame 102 with folded/flattened collar 103, hinge points 116, 120. FIG. 51 also shows folded/flattened inner regurgitation control component 137 with markers 144, and leaflets 258 mounted within folded/flattened inner frame 231.

Figure 52:
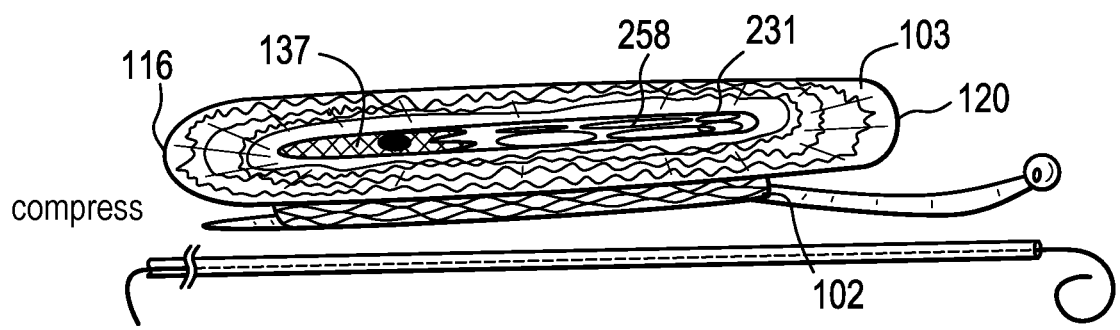
FIG. 52 is an illustration of a side perspective view of an orthogonally deliverable transcatheter heart valve in a vertically compressed configuration according to the invention.

FIG. 52 is an illustration of a side perspective view of an orthogonally deliverable transcatheter heart valve 100 in a vertically compressed configuration according to the invention. FIG. 52 shows outer frame 102 folded (z-axis) and compressed vertically (y-axis) with collar 103 folded (z-axis) and compressed (y-axis), along fold line between hinge points 116, 120. FIG. 52 also shows inner regurgitation control component 137, and leaflets 258 mounted within inner frame 231.

Figure 53:
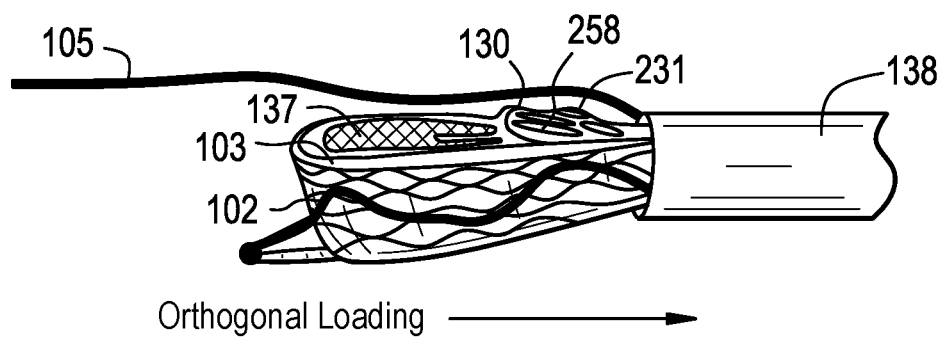
FIG. 53 is an illustration of a side perspective view of an orthogonally deliverable transcatheter heart valve partially loaded into a delivery catheter, according to the invention.

FIG. 53 is an illustration of a side perspective view of an orthogonally deliverable transcatheter heart valve 100 partially loaded into a delivery catheter 138, according to the invention. FIG. 53 shows outer frame 102, folded collar 103, inner regurgitation control component 137, and flow control component 130 having leaflets 258 and an inner frame 231.

Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by letters patent is set forth in the appended claims.

What is claimed:

1. A prosthetic heart valve, comprising:
    a valve frame defining a central channel extending along a central axis of the prosthetic heart valve, the valve frame including a distal subannular anchoring element and a proximal subannular anchoring element;
    a flow control component mounted within the central channel and configured to permit blood flow therethrough in a direction along the central axis; and
    a cinching system releasably attached to the proximal subannular anchoring element, a portion of the cinching system extending through the central channel and releasably attached to an interior of the valve frame in at least one location distal to the proximal subannular anchoring element,
    the prosthetic heart valve configured to be compressed along the central axis and a lateral axis perpendicular to the central axis to place the prosthetic heart valve in a compressed configuration for side-delivery into a heart via a delivery catheter during which each of the central axis and the lateral axis is perpendicular to a longitudinal axis of the delivery catheter, the prosthetic heart valve further configured to transition from the compressed configuration to an expanded configuration when the prosthetic heart valve is released from the delivery catheter into a chamber of the heart,
    the cinching system actuatable when the prosthetic heart valve is in the chamber of the heart such that a proximally directed force exerted on the cinching system transitions the proximal subannular anchoring element inwardly from a first configuration to a second configuration, in which the prosthetic heart valve is allowed to be seated in an annulus of a native heart valve, and
    the cinching system actuatable after the prosthetic heart valve is seated in the annulus to allow the proximal subannular anchoring element to transition outwardly toward the first configuration to at least partially secure the prosthetic heart valve in the annulus.

2. The prosthetic heart valve of claim 1, wherein the prosthetic heart valve in the expanded configuration has a first height along the central axis and a first lateral width along the lateral axis, and
    the prosthetic heart valve in the compressed configuration has a second height along the central axis less than the first height and a second lateral width along the lateral axis less than the first lateral width.

3. The prosthetic heart valve of claim 1, wherein the valve frame includes a valve body that defines the central channel, the valve body including a plurality of wire cells having an orientation that allows compression of the prosthetic heart valve along the central axis.

4. The prosthetic heart valve of claim 1, wherein the valve frame includes a valve body that defines the central channel and an atrial collar that is coupled along a supra-annular portion of the valve body, the distal subannular anchoring element extending from a distal subannular portion of the valve body, and the proximal subannular anchoring element extending from a proximal subannular portion of the valve body.

5. The prosthetic heart valve of claim 4, wherein after the cinching system is actuated to allow the proximal subannular anchoring element to transition toward the first configuration, the subannular anchoring elements are configured to be in contact with subannular tissue and the atrial collar is configured to be in contact with supra-annular tissue.

6. The prosthetic heart valve of claim 1, wherein the cinching system includes at least one tether releasably attached to the proximal subannular anchoring element,
    wherein the proximally directed force exerted to actuate the cinching system increases a tension along the at least one tether operable to pull the proximal subannular anchoring element inwardly to the second configuration, and
    wherein actuating the cinching system to allow the proximal subannular anchoring element to transition toward the first configuration includes releasing at least a portion of the tension along the at least one tether to allow the proximal subannular anchoring element to transition outwardly toward the first configuration.

7. A prosthetic heart valve, comprising:
    a valve frame having a valve body that defines a central channel extending along a central axis of the prosthetic heart valve, the valve frame including an atrial collar coupled to a top edge of the valve body, the atrial collar defining an opening;
    a flow control component mounted within the central channel and configured to permit blood flow therethrough in a direction along the central axis; and
    a cinching system releasably attached to a proximal subannular portion of the valve body, a portion of the cinching system extending through the opening of the atrial collar and attached to an interior of the valve body in at least one location distal to the proximal subannular portion of the valve body,
    the prosthetic heart valve configured to be compressed along the central axis and a lateral axis perpendicular to the central axis to place the prosthetic heart valve in a compressed configuration for side-delivery into a heart via a delivery catheter during which each of the central axis and the lateral axis is perpendicular to a longitudinal axis of the delivery catheter, the prosthetic heart valve further configured to transition from the compressed configuration to an expanded configuration when the prosthetic heart valve is released from the delivery catheter into a chamber of the heart,
    the cinching system actuatable when the prosthetic heart valve is in the chamber of the heart such that a proximally directed force exerted on the cinching system transitions the proximal subannular portion of the valve body inwardly from a first configuration to a second configuration, in which the prosthetic heart valve is allowed to be seated in an annulus of a native heart valve, and
    the cinching system actuatable after the prosthetic heart valve is seated in the annulus to allow the proximal subannular portion of the valve body to transition outwardly toward the first configuration to at least partially secure the prosthetic heart valve in the annulus.

8. The prosthetic heart valve of claim 7, wherein the prosthetic heart valve in the expanded configuration has a first height along the central axis, a first lateral width along a lateral axis perpendicular to the central axis, and the prosthetic heart valve in the compressed configuration has a second height along the central axis less than the first height and a second lateral width along the lateral axis less than the first lateral width.

9. The prosthetic heart valve of claim 7, wherein the valve body includes a plurality of wire cells having an orientation that allows compression of the prosthetic heart valve along the central axis.

10. The prosthetic heart valve of claim 7, wherein the atrial collar is configured to be in contact with supra-annular tissue when the prosthetic heart valve is seated in the annulus.

11. The prosthetic heart valve of claim 10, wherein the proximal subannular portion of the valve body includes a proximal subannular anchoring element configured to be in contact with subannular tissue after the cinching system is actuated to allow the proximal subannular portion to transition toward the first configuration.

12. The prosthetic heart valve of claim 7, wherein the cinching system includes at least one tether releasably attached to the proximal subannular portion of the valve body,
  wherein the proximally directed force exerted to actuate the cinching system increases a tension along the at least one tether operable to pull the proximal subannular portion of the valve body inwardly to the second configuration, and
  wherein actuating the cinching system to allow the proximal subannular portion of the valve body to transition toward the first configuration includes releasing at least a portion of the tension along the at least one tether to allow the proximal subannular portion of the valve body to transition outwardly toward the first configuration.

* * * * *